(12) United States Patent
Or et al.

(10) Patent No.: US 6,764,996 B1
(45) Date of Patent: Jul. 20, 2004

(54) 9A-AZALIDES WITH ANTIBACTERIAL ACTIVITY

(75) Inventors: Yat Sun Or, Cambridge, MA (US); Robert F. Keyes, Pleasant Prairie, WI (US); Zhenkun Ma, Gurnee, IL (US)

(73) Assignee: Abbott Laboratories, Abbott Park, IL (US)

(*) Notice: Subject to any disclaimer, the term of this patent is extended or adjusted under 35 U.S.C. 154(b) by 0 days.

(21) Appl. No.: 09/624,849

(22) Filed: Jul. 25, 2000

Related U.S. Application Data

(63) Continuation of application No. 60/150,490, filed on Aug. 24, 1999.

(51) Int. Cl.[7] .................. C07D 413/12; C07D 413/14; A61K 31/70; A61P 31/04
(52) U.S. Cl. ................. 514/29; 540/467; 540/468; 514/375; 514/450; 536/7.4
(58) Field of Search ............... 540/468, 467; 514/450, 375, 29; 536/7.4

(56) References Cited

U.S. PATENT DOCUMENTS 4,328,334 A * 5/1982 Kobrehel et al. ............ 536/7.4

(List continued on next page.)

FOREIGN PATENT DOCUMENTS

EP        0 109 253 A2    5/1984

(List continued on next page.)

OTHER PUBLICATIONS

Wilkening, R. R., et al.: "Novel Transannular Rearrange- (List continued on next page.)

Primary Examiner—Mark L. Berch
Assistant Examiner—Kahsay Habte
(74) Attorney, Agent, or Firm—B. Gregory Donner

(57) ABSTRACT

Compounds of formula (I)

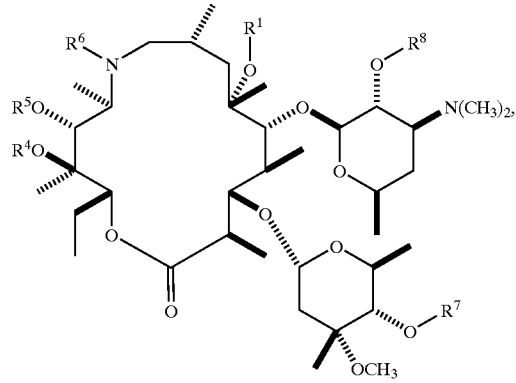

(I)

formula (II)

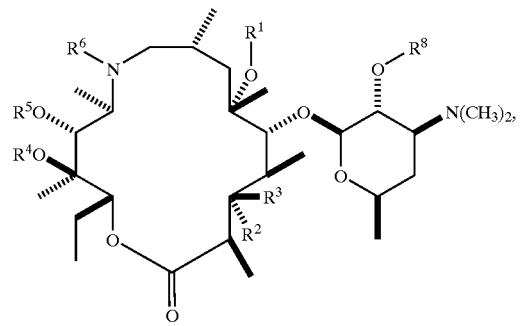

(II)

formula (III)

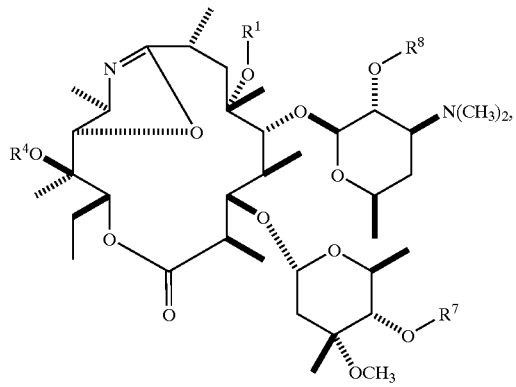

(III)

and
formula (IV)

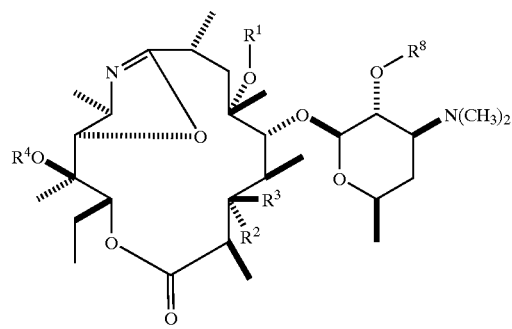

(IV)

or pharmaceutically acceptable salts or prodrugs thereof, are antibacterial agents. Compositions containing the compounds, processes for making the compounds, synthetic intermediates employed in the processes, and methods for treatment and prevention of bacterial infections are disclosed.

19 Claims, No Drawings

U.S. PATENT DOCUMENTS

| | | | |
|---|---|---|---|
| 4,474,768 A | 10/1984 | Bright | 424/180 |
| 4,517,359 A | 5/1985 | Kobrehel et al. | 536/7.4 |
| 4,990,602 A | 2/1991 | Morimoto et al. | 536/7.4 |
| 5,686,587 A | 11/1997 | Yang | 514/29 |
| 5,866,549 A | 2/1999 | Or et al. | 514/29 |

FOREIGN PATENT DOCUMENTS

| | | |
|---|---|---|
| EP | 0 259 789 A2 | 3/1988 |
| WO | 9856801 | 12/1998 |
| WO | 9856802 | 12/1998 |
| WO | 9900124 | 1/1999 |
| WO | 9900125 | 1/1999 |

OTHER PUBLICATIONS ments of Azaliden Iminoethers" Tetrahedron, NL, Elsevier Science Publishers, Amsterdam, vol. 53, No. 50, Dec. 15, 1997, pp. 16923–16944, XP004106498, ISSN: 0040–4020, p. 16927, compounds 17,19.

9A-AZALIDES WITH ANTIBACTERIAL ACTIVITY

REFERENCE TO RELATED APPLICATION

This application is a conversion of U.S. Provision Patent Application No. 60/150,490, filed on Aug. 24, 1999.

TECHNICAL FIELD

The instant invention relates to 9a-azalides which are antibacterial agents, compositions containing the compounds, processes for making the compounds, synthetic intermediates employed in the processes, and methods for treatment and prevention of bacterial infections.

BACKGROUND OF THE INVENTION

Macrolide antibacterial agents are widely used to treat and prevent bacterial infections. However, the discovery of bacterial strains which have resistance or insufficient susceptibility to macrolide antibacterial agents has promoted development of compounds with modified or improved profiles of antibiotic activity. One such class of compounds are azalides such as azithromycin, referred to in U.S. Pat. Nos. 4,474,768 and 4,517,359. Azalides are macrolide antibacterial agents with a core ring structurally similar to the erythronolide A or B ring except for the presence of a substituted or unsubstituted nitrogen moiety at the 9a position. Because of the potential for azalides to display modified or improved profiles of antibiotic activity, they are the subject of current research for their clinical potential.

PCT Application WO 98/56801, published Dec. 17, 1998 discloses a series of 9a-(N(alkyl))-azalide erythromycin A derivatives and a series of 9a-(N-(alkyl))-azalide 6-O-methylerythromycin A derivatives.

PCT Application WO 98/56802, published Dec. 17, 1998 discloses a series of 9a-(N(H))-azalide erythromycin A derivatives and a series of 9a-(N(H))-azalide 6-O-methylerythromycin A derivatives.

PCT Application WO 99/00124, published Jan. 7, 1999, discloses a series of 9a-(N($R_n$))-azalide 3-thioxoerythromycin A derivatives and a series of 9a-(N(R″))-azalide 6-O-methyl-3-oxoerythromycin A derivatives, wherein $R_n$ is an optionally substituted alkyl or heteroalkyl.

PCT Application WO 99/00125, published Jan. 7, 1999, discloses a series of 9a-(N($R_n$))-azalide 3-oxoerythromycin A derivatives and a series of 9a-(N($R_n$))-azalide 6-O-methyl-3-oxoerythromycin A derivatives, wherein ($R_n$ is an optionally substituted alkyl or heteroalkyl.

U.S. Pat. No. 5,686,587 discloses a synthesis of azithromycin comprising introducing a 9a-(N(H))-moiety to erythromycin A by oxime formation, Beckman rearrangement, reduction, and methylation.

SUMMARY OF THE INVENTION

In one embodiment of the present invention are disclosed compounds of formula (I)

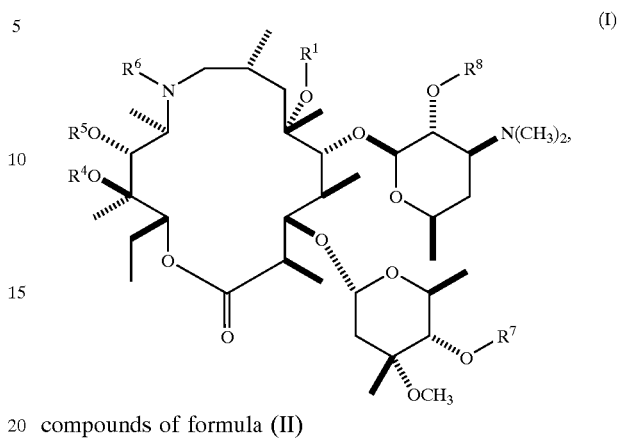

(I)

compounds of formula (II)

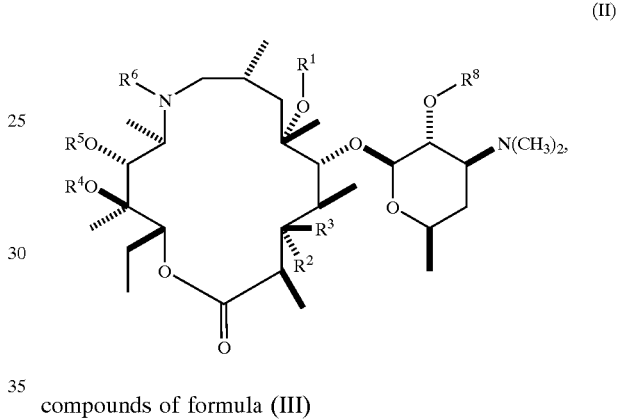

(II)

compounds of formula (III)

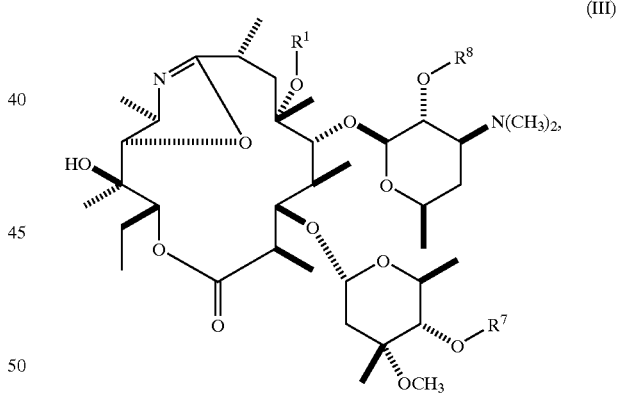

(III)

and compounds of formula (IV)

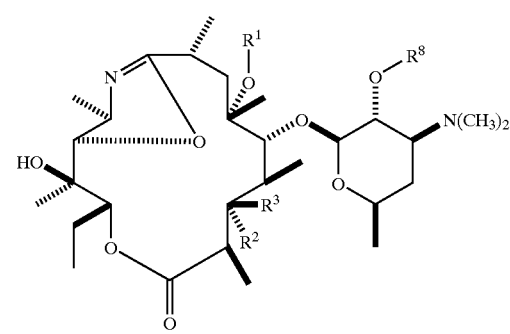

(IV)

or pharmaceutically acceptable salts or prodrugs thereof, wherein, in formulas (I)–(IV), $R^1$ and $R^6$ are independently selected from the group consisting of
(1) hydrogen,
(2) —$C_1$–$C_{12}$-alkyl,
(3) —$C_3$–$C_{12}$-alkenyl, and
(4) —$C_3$–$C_{12}$-alkynyl,
wherein (2)–(4) can be optionally substituted with one, two, or three substituents independently selected from the group consisting of
(a) halogen,
(b) —$OR^9$, wherein $R^9$ is selected from the group consisting of
(i) hydrogen,
(ii) —$C_1$–$C_{12}$-alkyl,
(iii) —$C_2$–$C_{12}$-heteroalkyl,
wherein (ii) and (iii) can be optionally substituted with one, two, or three substituents independently selected from the group consisting of
(1') aryl,
(2') substituted aryl,
(3') heteroaryl,
and
(4') substituted heteroaryl,
(iv) aryl,
(v) substituted aryl,
(vi) heteroaryl,
and
(vii) substituted heteroaryl,
(c) —$NR^{11}R^{12}$, wherein $R^{11}$ and $R^{12}$ are independently selected from the group consisting of
(i) hydrogen,
(ii) —$C_1$–$C_{12}$-alkyl,
(iii) —$C_2$–$C_{12}$-heteroalkyl,
wherein (ii) and (iii) can be optionally substituted with one, two, or three substituents independently selected from the group consisting of
(1') aryl,
(2') substituted aryl,
(3') heteroaryl,
and
(4') substituted heteroaryl,
(iv) aryl,
(v) substituted aryl,
(vi) heteroaryl,
and
(vii) substituted heteroaryl,
or
$R^{11}$ and $R^{12}$, together with the atom to which they are attached, form a heterocycloalkyl ring, wherein the heterocycloalkyl ring can be optionally substituted,
(d) =N—O—$R^9$, wherein $R^9$ is defined above,
(e) aryl,
(f) substituted aryl,
(g) heteroaryl,
(h) substituted heteroaryl,
(i) —$C_3$–$C_8$-cycloalkyl,
(j) substituted —$C_3$–$C_8$-cycloalkyl,
(k) heterocycloalkyl,
(l) substituted heterocycloalkyl,
(m) —$NHC(O)R^9$, wherein $R^9$ is defined above,
(n) —$NHC(O)OR^{10}$, wherein $R^{10}$ is selected from the group consisting of
(i) —$C_1$–$C_{12}$-alkyl,
(ii) —$C_1$–$C_{12}$-heteroalkyl,
wherein (i) and (ii) can be optionally substituted with one, two, or three substituents independently selected from the group consisting of
(1') aryl,
(2') substituted aryl,
(3') heteroaryl,
and
(4') substituted heteroaryl,
(iii) aryl,
(iv) substituted aryl,
(v) heteroaryl,
and
(vi) substituted heteroaryl,
(o) —$NHC(O)NR^{11}R^{12}$, wherein $R^{11}$ and $R^{12}$ are defined above,
(p) —$OC(O)R^{10}$, wherein $R^{10}$ is defined above,
(q) —$OC(O)OR^{10}$, wherein $R^{10}$ is defined above,
(r) —$OC(O)NR^{11}R^{12}$, wherein $R^{11}$ and $R^{12}$ are defined above,
(s) —$C(O)R^9$, wherein $R^9$ is defined above,
(t) —$CO_2R^9$, wherein $R^9$ is defined above,
and
(u) —$C(O)NR^{11}R^{12}$, wherein $R^{11}$ and $R^{12}$ are defined above;
$R^2$ is hydrogen;
$R^3$ is —$OR^{13}$, wherein $R^{13}$ is selected from the group consisting of
(1) hydrogen,
(2) —$C(O)R^9$, wherein $R^9$ is defined above,
(3) —$CO_2R^{10}$, wherein $R^{10}$ is defined above,
and
(4) —$C(O)NR^{11}R^{12}$, wherein $R^{11}$ and $R^{12}$ are defined above;
or
$R^2$ and $R^3$ together are oxo;
$R^4$ and $R^5$ are hydrogen;
or
$R^4$ and $R^5$ together are —C(O)— or —$(CH_2)_x$—, wherein x is one, two, or three;
or
$R^5$ and $R^6$ together are —C(O)— or —$(CH_2)_x$—, wherein x is defined above;
$R^7$ is selected from the group consisting of
(1) hydrogen,
(2) —$C_1$–$C_{12}$-alkyl,
(3) —$C_3$–$C_{12}$-alkenyl,
(4) —$C_3$–$C_{12}$-alkynyl,
(5) —$C_2$–$C_{12}$-heteroalkyl,
(6) —$C_4$–$C_{12}$-heteroalkenyl,
(7) —$C_4$–$C_{12}$-heteroalkynyl,
wherein (2)–(7) can be optionally substituted with one, two, or three substituents independently selected from the group consisting of
(a) halo,
(b) hydroxy,
(c) —$NR^{11}R^{12}$, wherein $R^{11}$ and $R^{12}$ are defined above,
(d) aryl,
(e) substituted aryl,
(f) heteroaryl,
and
(g) substituted heteroaryl,
(8) —$C(O)R^9$, wherein $R^9$ is defined above,
(9) —$CO_2R^9$, wherein $R^9$ is defined above, and

(11) —C(O)NR$^{11}$R$^{12}$, wherein R$^{11}$ and R$^{12}$ are defined above;

and

R$^8$ is hydrogen or a hydroxy protecting group;

with the proviso that when R$^2$ and R$^3$ together are oxo, R$^1$ is other than hydrogen or unsubstituted methyl.

In another embodiment of the present invention are disclosed pharmaceutical compositions comprising a pharmaceutically effective amount of the compounds in combination with a pharmaceutically acceptable carrier.

In still another embodiment of the present invention are disclosed methods of treating a bacterial infection in a mammal in need of such treatment which comprises administering to the mammal a therapeutically effective amount of the compounds.

In still yet another embodiment of the present invention is disclosed a method for preparing the compounds, the method comprising (a) reacting compounds of formula (Ia)

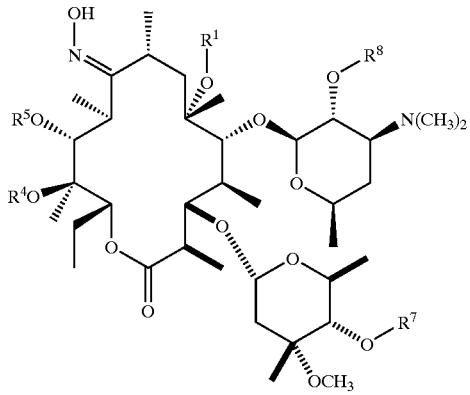

(Ia)

or compounds of formula (Ib)

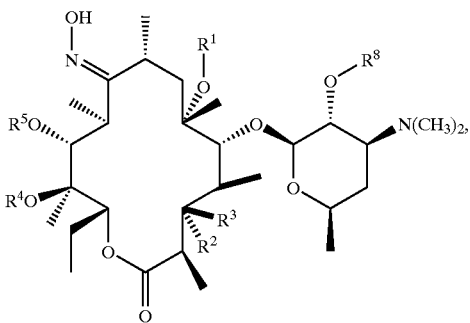

(Ib)

wherein R$^1$, R$^2$, R$^3$, R$^4$, R$^5$, R$^7$, and R$^1$ are defined above, with an oxime activating agent;

(b) optionally reacting the product from step (a) with a reducing agent;

(c) optionally alkylating the product from step (b); and (d) optionally deprotecting the product from step (c).

DETAILED DESCRIPTION OF THE INVENTION

The term "alkenyl," as used herein, refers to a monovalent straight or branched chain group containing at least one carbon-carbon double bond. The alkenyl groups of this invention can be optionally substituted.

The term "alkyl," as used herein, refers to saturated, straight or branched chain hydrocarbon radicals. Examples of alkyl radicals include methyl, ethyl, propyl, iso-propyl, n-butyl, tert-butyl, neo-pentyl, and n-hexyl. The alkyl groups of this invention can be optionally substituted.

The term "—C$_1$–C$_3$-alkylamino," as used herein, refers to a amino group, as defined herein wherein one hydrogen atom is replaced by a —C$_1$–C$_3$-alkyl group. Examples of —C$_1$–C$_3$-alkylamino include methylamine, ethylamine, propylamine, and iso-propylamine.

The term "—C$_1$–C$_3$-alkylthio," as used herein, refers to a —C$_1$–C$_3$-alkyl group, as defined herein, attached to the parent molecular group through a sulfur atom. Examples of —C$_1$–C$_3$-alkylthio include methyl sulfide, ethyl sulfide, propyl sulfide, and iso-propyl sulfide.

The term "alkoxy," as used herein, refers to an alkyl group, as previously defined, attached to the parent molecular group through an oxygen atom. Examples of alkoxy include methoxy, ethoxy, propoxy, isopropoxy, n-butoxy, tert-butoxy, neo-pentoxy and n-hexoxy. The alkoxy groups of this invention can be optionally substituted.

The term "alkynyl," as used herein, refers to a monovalent straight or branched chain group of two to six carbon atoms containing at least one carbon-carbon triple bond. Examples of alkynyl include ethynyl, propynyl, and butynyl. The alkynyl groups of this invention can be optionally substituted.

The term "amino," as used herein, refers to —NH$_2$.

The term "aprotic solvent," as used herein, refers to a solvent that is relatively inert to proton activity, i.e., not acting as a proton donor. Examples include hydrocarbons such as hexane and toluene, halogenated hydrocarbons such as dichloromethane, ethylene chloride, and chloroform, heterocyclic compounds such as tetrahydrofuran and N-methylprrolidinone, and ethers such as diethyl ether, bis-methoxymethyl ether. Such compounds are well known to those skilled in the art, and it will be obvious to those skilled in the art that individual solvents or mixtures thereof can be preferred for specific compounds and reaction conditions, depending upon such factors as the solubility of reagents, reactivity of reagents and preferred temperature ranges, for example. Further discussions of aprotic solvents can be found in organic chemistry textbooks or in specialized monographs, for example: *Organic Solvents Physical Properties and Methods of Purification*, 4th ed., edited by John A. Riddick, et al., Vol. II, in the Techniques of Chemistry Series, John Wiley & Sons, NY, 1986, the relevant portions of which are incorporated herein by reference.

The term "aryl" as used herein refers to unsubstituted carbocyclic aromatic groups including phenyl, naphthyl, and anthracenyl.

The term "arylamino," as used herein, refers to a amino group, as defined herein wherein one hydrogen atom is replaced by an aryl group, as defined herein.

The term "aryloxy," as used herein, refers to an aryl group, as defined herein, attached to the parent molecular group through an oxygen atom.

The term "arylthio," as used herein, refers to an aryl group, as defined herein, attached to the parent molecular group through a sulfur atom.

The term "azido," as used herein, refers to —N$_3$.

The term "benzyl," as used herein, refers to —CH$_2$C$_6$H$_5$.

The term "benzyloxy," as used herein, refers to a benzyl group, as defined herein, attached to the parent molecular group through an oxygen atom.

The term "benzylamino," as used herein, refers to a amino group, as defined herein wherein one hydrogen atom is replaced by a benzyl group, as defined herein.

The term "benzylthio," as used herein, refers to an benzyl group, as defined herein, attached to the parent molecular group through a sulfur atom.

The term "carboxaldehyde," as used herein, refers to —CHO.

The term "cyano," as used herein, refers to —CN.

The term "cycloalkyl," as used herein, refers to saturated carbocyclic groups having three to seven carbons such as cyclopropyl, cyclobutyl, cyclopentyl, cyclohexyl, and cycloheptyl.

The term "halo," as used herein, refers to —F, —Cl, —Br, and —I. The term "heteroalkenyl," as used herein, refers to an alkenyl group having from four to twelve atoms, wherein at least atom is replaced with a group selected from —O—, =N—, —N(H)—, —N($CH_3$)—, —C(O)—, —S(O)$_n$—, or a combination thereof, and the remaining atoms are carbon. The heteroalkenyl groups of this invention can be optionally substituted.

The term "heteroalkyl," as used herein, refers to an alkyl group having from two to twelve atoms, wherein at least atom is replaced with a group selected from —O—, =N—, —N(H)—, —N($CH_3$)—, —C(O)—, —S(O)$_n$, or a combination thereof, and the remaining atoms are carbon. The heteroalkyl groups of this invention can be optionally substituted.

The term "heteroalkynyl," as used herein, refers to an alkynyl group having from four to twelve atoms, wherein at least atom is replaced with a group selected from —O—, =N—, —N(H)—, —N($CH_3$)—, —C(O)—, —S(O)$_n$—, or a combination thereof, and the remaining atoms are carbon. The heteroalkynyl groups of this invention can be optionally substituted.

The term "heteroaryl," as used herein, refers to a cyclic aromatic group having five or six ring atoms wherein at least one ring atom is selected from the group consisting of oxygen, sulfur, and nitrogen, and the remaining ring atoms are carbon. The nitrogen atoms can optionally be quaternized, and the sulfur atoms can optionally be oxidized. Heteroaryl groups of this invention include those derived from furan, imidazole, isothiazole, isoxazole, oxadiazole, oxazole, 1,2,3-oxadiazole, pyrazine, pyrazole, pyridazine, pyridine, pyrimidine, pyrroline, quinoline, thiazole, 1,3,4-thiadiazole, thiene, triazole, and tetrazole.

The term "heteroarylamino," as used herein, refers to a amino group, as defined herein wherein one hydrogen atom is replaced by a heteroaryl group, as defined herein.

The term "heteroaryloxy," as used herein, refers to a heteroaryl group, as defined herein, attached to the parent molecular group through an oxygen atom.

The term "heteroarylthio," as used herein, refers to a heteroaryl group, as defined herein, attached to the parent molecular group through a sulfur atom.

The term "heterocycloalkyl" as used herein, refers to a non-aromatic five-, six- or seven-membered ring or a bi- or tri-cyclic group comprising fused six-membered rings having between one and three heteroatoms independently selected from oxygen, sulfur and nitrogen wherein each 5-membered ring has zero to one double bonds and each six-membered ring has zero to 2 double bonds. The nitrogen and sulfur heteroatoms can optionally be oxidized, the nitrogen heteroatom can optionally be quaternized, and any of the above heterocyclic rings can be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The heterocycloalkyl groups of this invention can be optionally substituted with one, two, three, or four substituents independently selected from —F, —Cl, —Br, —I, —OH, —$NO_2$, —CN, —C(O)—$C_1$-$C_6$-alkyl, —C(O)-aryl, —C(O)-heteroaryl, —$CO_2$-alkyl, —$CO_2$-aryl, —$CO_2$-heteroaryl, —$CONH_2$, —CONH—$C_1$-$C_6$-alkyl, —CONH-aryl, —CONH-heteroaryl, —OC(O)—$C_1$-$C_6$-alkyl, —OC(O)-aryl, —OC(O)-heteroaryl, —$OCO_2$-alkyl, —$OCO_2$-aryl, —$OCO_2$-heteroaryl, —$OCONH_2$, —OCONH—$C_1$-$C_6$-alkyl, —OCONH-aryl, —OCONH-heteroaryl, —NHC(O)—$C_1$-$C_6$-alkyl, —NHC(O)-aryl, —NHC(O)-heteroaryl, —$NHCO_2$-alkyl, —$NHCO_2$-aryl, —$NHCO_2$-heteroaryl, —$NHCONH_2$, —NHCONH—$C_1$-$C_6$-alkyl, —NHCONH-aryl, —NHCONH-heteroaryl, —$SO_2$—$C_1$-$C_6$-alkyl, —$SO_2$-aryl, —$SO_2$-heteroaryl, —$SO_2NH_2$, —$SO_2$NH—$C_1$-$C_6$-alkyl, —$SO_2$NH-aryl, —$SO_2$NH-heteroaryl, —$C_1$-$C_6$-alkyl, —$C_3$-$C_6$-cycloalkyl, —$CF_3$, —$CH_2CF_3$, —$CHCl_2$, —$CH_2OH$, —$CH_2CH_2OH$, —$CH_2NH_2$, —$CH_2SO_2CH_3$, aryl, heteroaryl, benzyl, benzyloxy, aryloxy, heteroaryloxy, —$C_1$-$C_6$-alkoxy, methoxymethoxy, methoxyethoxy, amino, benzylamino, arylamino, heteroarylamino, —$C_1$-$C_3$-alkylamino, thio, arylthio, heteroarylthio, benzylthio, —$C_1$-$C_6$-alkylthio, or methylthiomethyl.

The term "hydroxy," as used herein, refers to —OH.

The term "hydroxy protecting group", as used herein, refers to an easily removable group to which are known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf. for example, T. H. Greene and P. G. M. Wuts, *Protective Groups in Organic Synthesis*, 2nd edition, John Wiley & Sons, New York (1991), the relevant portions of which are incorporated herein by reference. Examples of hydroxy-protecting groups include, methylthiomethyl, tert-dimethylsilyl, tert-butyldiphenylsilyl, acyl substituted with an aromatic group, and the like.

The term "methoxymethoxy," as used herein, refers to —$OCH_2OCH_3$.

The term "methoxyethoxy," as used herein, refers to —$OCH_2OCH_2CH_3$.

The term "methylthiomethyl," as used herein, refers to —$CH_2SCH_3$.

The term "oxo," as used herein, refers to a group formed by the replacement of two hydrogen atoms on the same carbon atom of an alkyl group, as defined above, with a single oxygen atom and is exemplified by a carbonyl group.

A the term "protected hydroxy" refers to a hydroxy group protected with a hydroxy protecting group, as defined above, such as benzoyl, acetyl, trimethylsilyl, triethylsilyl, or methoxymethyl groups.

The term "substituted aryl," as used herein, refers to an aryl group, as defined herein, substituted by independent replacement of one, two or three of the hydrogen atoms thereon with —F, —Cl, —Br, —I, —OH, —$NO_2$, —CN, —C(O)—$C_1$-$C_6$-alkyl, —C(O)-aryl, —C(O)-heteroaryl, —$CO_2$-alkyl, —$CO_2$-aryl, —$CO_2$-heteroaryl, —$CONH_2$, —CONH—$C_1$-$C_6$-alkyl, —CONH-aryl, —CONH-heteroaryl, —OC(O)—$C_1$-$C_6$-alkyl, —OC(O)-aryl, —OC(O)-heteroaryl, —$OCO_2$-alkyl, —$OCO_2$-aryl, —$OCO_2$-heteroaryl, —$OCONH_2$, —OCONH—$C_1$-$C_6$-alkyl, —OCONH-aryl, —OCONH-heteroaryl, —NHC(O)—$C_1$-$C_6$-alkyl, —NHC(O)-aryl, —NHC(O)-heteroaryl, —$NHCO_2$-alkyl, —$NHCO_2$-aryl, —$NHCO_2$-heteroaryl, —$NHCONH_2$, —NHCONH—$C_1$-$C_6$-alkyl, —NHCONH-aryl, —NHCONH-heteroaryl, —$SO_2$—$C_1$-$C_6$-alkyl, —$SO_2$-aryl, —$SO_2$-heteroaryl, —$SO_2NH_2$, —$SO_2$NH—$C_1$-$C_6$-alkyl, —$SO_2$NH-aryl, —$SO_2$NH-heteroaryl, —$C_1$-$C_6$-alkyl, —$C_3$-$C_6$-cycloalkyl, —$CF_3$, —$CH_2CF_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxylmethoxymethoxy, methoxyethoxy, amino, benzylamino, arylamino, heteroarylamino, —C$_1$–C$_3$-alkylamino, thio, arylthio, heteroarylthio, benzylthio, —C$_1$–C$_6$-alkylthio, or methylthiomethyl.

The term "substituted heteroaryl" as used herein refers to a heteroaryl group as defined herein substituted by independent replacement of one, two or three of the hydrogen atoms thereon with —F, —Cl, —Br, —I, —OH, —NO$_2$, —CN, —C(O)—C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$–C$_6$-alkyl, —CONH-aryl, —CONH-heteroaryl, —OC(O)—C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$–C$_6$-alkyl, —OCONH-aryl, —OCONH-heteroaryl, —NHC(O)—C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$–C$_6$-alkyl, —NHCONH-aryl, —NHCONH-heteroaryl, —SO$_2$—C$_1$–C$_6$-alkyl, —SO$_2$-aryl, —SO$_2$-heteroaryl, —SO$_2$NH$_2$, —SO$_2$NH—C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxy, methoxymethoxy, methoxyethoxy, amino, benzylamino, arylamino, heteroarylamino, —C$_1$–C$_3$-alkylamino, thio, arylthio, heteroarylthio, benzylthio, —C$_1$–C$_6$-alkylthio, or methylthiomethyl.

The term "substituted heterocycloalkyl," as used herein, refers to a heterocycloalkyl group, as defined above, substituted by independent replacement of one, two or three of the hydrogen atoms thereon with —F, —Cl, —Br, —I, —OH, —NO$_2$, —CN, —C(O)—C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$–C$_6$-alkyl, —CONH-aryl, —CONH-heteroaryl, —OC(O)—C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$–C$_6$-alkyl, —OCONH-aryl, —OCONH-heteroaryl, —NHC(O)—C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$–C$_6$-alkyl, —NHCONH-aryl, —NHCONH-heteroaryl, —SO$_2$—C$_1$–C$_6$-alkyl, —SO$_2$-aryl, —SO$_2$-heteroaryl, —SO$_2$NH$_2$, —SO$_2$NH—C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, —C$_1$–C$_3$-alkylamino, thio, arylthio, heteroarylthio, benzylthio, alkylthio, or methylthiomethyl.

The term "thio," as used herein, refers to —SH.

Numerous asymmetric centers exist in the compounds of the present invention. Except where otherwise noted, the present invention contemplates the various stereoisomers and mixtures thereof. Accordingly, whenever a bond is represented by a wavy line or a straight line, it is intended that a mixture of stereo-orientations or an individual isomer of unassigned orientation can be present.

The term "pharmaceutically acceptable prodrugs," as used herein refers to, those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "prodrug," as used herein, represents compounds which are rapidly transformed in vivo to parent compounds defined above, for example, by hydrolysis in blood. A thorough discussion is provided in T. Higuchi and V. Stella, Prodrugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, the relevant portions of which are incorporated herein by reference.

The term "pharmaceutically acceptable salt," as used herein, refers to those salts which are, within the scope of sound medical judgment, suitable for use in contact with the tissues of humans and lower animals without undue toxicity, irritation, and allergic response and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66:1–19 (1977), the relevant portions of which are incorporated herein by reference. The salts can be prepared in situ during the final isolation and purification of the compounds of the invention or separately by reacting a free base group with a suitable organic acid. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laureate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, and valerate. Representative alkali or alkaline earth metal salts include sodium, lithium, potassium, calcium, and magnesium. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laureate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type can also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as can be required.

Ophthalmic formulation, ear drops, eye ointments, powders and solutions are also contemplated as being within the scope of this invention.

The ointments, pastes, creams and gels can contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions can contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Preferred compounds of the invention include:

Compound of formula (II): $R^2$ is hydrogen, $R^3$ is —$OR^{13}$, and $R^{13}$ is hydrogen.

Compound of formula (II): $R^2$ and $R^3$ together are oxo.

Compound of formula (I): $R^4$ and $R^5$ are hydrogen.

Compound of formula (I): $R^4$ and $R^5$ are hydrogen.

Compound of formula (II): $R^4$ and $R^5$ together are —C(O)—.

Compound of formula (I): $R^6$ is hydrogen.

Compound of formula (I): $R^6$ is methyl.

Compound of formula (II): $R^6$ is methyl.

Compound of formula (I): $R^1$ is —$CH_2$—CH=$CH_2$.

Compound of formula (II): $R^1$ is —$CH_2$—CH=$CH_2$.

Compound of formula (I): $R^1$ is —$CH_2$—CH=CH-(3-quinolinyl).

and

Compound of formula (II): $R^1$ is —$CH_2$—CH=CH-(3-quinolinyl).

Specific compounds of the invention include:

Compound of formula (III): $R^1$ is —$CH_2$CH=$CH_2$, $R^4$ is hydrogen, $R^7$ is hydrogen, $R^8$ is hydrogen, Compound of formula (I): $R^1$ is —$CH_2$CH=$CH_2$, $R^4$ is hydrogen, $R^5$ is hydrogen, $R^6$ is hydrogen, $R^7$ is hydrogen, $R^8$ is hydrogen, Compound of formula (I): $R^1$ is —$CH_2$CH=$CH_2$, $R^4$ is hydrogen, $R^5$ is hydrogen, $R^6$ is methyl, $R^7$ is hydrogen, $R^8$ is hydrogen, Compound of formula (II): $R^1$ is —$CH_2$CH=CH-(3-quinolinyl), $R^2$ and $R^3$ together are oxo, $R^4$ is hydrogen, $R^5$ is hydrogen, $R^6$ is methyl, $R^8$ is hydrogen, Compound of formula (II): $R^1$ is —$CH_2$CH=CH-(3-quinolinyl), $R^2$ and $R^3$ together are oxo, $R^4$ is hydrogen, $R^5$ is hydrogen, $R^6$ is methyl, $R^8$ is hydrogen, Compound of formula (II): $R^1$ is —$CH_2$CH=CH-(3-quinolinyl), $R^2$ and $R^3$ together are oxo, $R^4$ and $R^5$ together are —C(O)—, $R^6$ is methyl, $R^8$ is —C(O)$CH_3$, and Compound of formula (I): $R^1$ is —$CH_2$CH=CH-(3-quinolinyl), $R^4$ is hydrogen, $R^5$ is hydrogen, $R^6$ is methyl, $R^7$ is hydrogen, $R^8$ is hydrogen.

Determination of Biological Activity

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1, demonstrate the antibacterial activity of the compounds of the invention.

| Microorganism | Code |
|---|---|
| Staphylococcus aureus ATCC 6538P | AA |
| Staphylococcus aureus A-5177 | BB |
| Staphylococcus aureus A-5278 | CC |
| Staphylococcus aureus CMX 642A | DD |

-continued

| Microorganism | Code |
| --- | --- |
| Staphylococcus aureus NCTC 10649M | EE |
| Staphylococcus aureus CMX 553 | FF |
| Staphylococcus aureus 1775 | GG |
| Staphylococcus epidermidis 3519 | HH |
| Enterococcusfaecium ATCC X043 | II |
| Streptococcus bovis A-5169 | JJ |
| Streptococcus agalactiae CMX 508 | KK |
| Streptococcus pyogenes EES61 | LL |
| Streptococcus pyogenes 930 | MM |
| Streptococcus pyogenes PIU 2548 | NN |
| Micrococcusluteus ATCC 9341 | OO |
| Micrococcusluteus ATCC 4698 | PP |
| Escherichiacoli JUHL | QQ |
| Escherichiacoli SS | RR |
| Escherichiacoli DC-2 | SS |
| Candida albicans CCH 442 | TT |
| Mycobacterium smegmatis ATCC 114 | UU |
| Nocardia Asteroides ATCC 99700 | VV |
| HaemophilisInfluenzae DILL AMP R | WW |
| Streptococcus Pneumonia ATCC 6303 | XX |
| Streptococcus Pneumonia GYR 1171 | YY |
| Streptococcus Pneumonia 5979 | ZZ |
| Streptococcus Pneumonia 5649 | ZA |

TABLE 1

Antibacterial Activity (MIC's) of Selected Compounds

| | Ery. A standard | Example 2 | Example 3 | Example 4 | Example 5 | Example 6 | Example 7 |
| --- | --- | --- | --- | --- | --- | --- | --- |
| AA | 0.2 | 0.2 | 0.2 | 0.39 | 0.2 | 0.2 | 0.1 |
| BB | 3.1 | 12.5 | 12.5 | 6.2 | 12.5 | 12.5 | 3.1 |
| CC | >100 | >100 | >100 | >100 | >100 | >100 | >100 |
| EE | 0.39 | 0.39 | 0.39 | 0.39 | 0.39 | 0.39 | 0.39 |
| GG | >100 | >100 | >100 | >100 | >100 | >100 | >100 |
| HH | 0.39 | 0.2 | 0.39 | 0.39 | 0.2 | 0.2 | 0.2 |
| JJ | 0.02 | 0.02 | 0.05 | 0.02 | 0.02 | 0.02 | 0.1 |
| KK | 0.05 | 0.05 | 0.1 | 0.05 | 0.05 | 0.05 | 0.1 |
| LL | 0.05 | 0.05 | 0.05 | 0.05 | 0.05 | 0.05 | 0.05 |
| MM | >100 | >100 | >100 | >100 | >100 | >100 | >100 |
| NN | 6.2 | 6.2 | 6.2 | 6.2 | 6.2 | 6.2 | 6.2 |
| PP | 0.2 | 0.39 | 0.39 | 0.39 | 0.39 | 0.39 | 0.2 |
| QQ | >100 | 50 | 50 | 50 | 50 | 50 | 100 |
| RR | 0.78 | 0.78 | 0.39 | 0.78 | 0.78 | 0.78 | 0.39 |
| TT | >100 | >100 | >100 | >100 | >100 | >100 | >100 |
| UU | 3.1 | 6.2 | 6.2 | 6.2 | 6.2 | 6.2 | 6.2 |
| VV | 0.1 | 0.1 | 0.1 | 0.05 | 0.1 | 0.1 | 0.05 |
| WW | 4 | 8 | 8 | 4 | 4 | 4 | 8 |
| XX | 0.06 | 0.06 | 0.06 | 0.03 | 0.06 | 0.06 | 0.12 |
| YY | 0.06 | 0.06 | 0.06 | 0.03 | 0.03 | 0.03 | 0.12 |
| ZZ | >128 | >128 | >128 | >128 | >128 | >128 | >128 |
| ZA | 16 | 16 | 8 | 8 | 8 | 8 | 16 |

Synthetic Methods

Abbreviations

Abbreviations which have been used in the descriptions of the schemes and the examples that follow are: Ac for acetate; Bz for benzoyl; dba for dibenzylidine acetone; CDI for carbonyldiimidazole; DCM for dichloromethane; DMA for N,N-dimethylacetamide; DMAP for 4-(N,N-dimethylamino)pyridine; DME for dimethoxyethane; DMF for N,N-dimethylformamide; DMS for dimethylsulfide; DMSO for dimethylsulfoxide; dppb for 1,4-bis (diphenylphosphino)butane; EDCI for 1-[3-(dimethylamino)propyl]-3-ethylcarbodiimide hydrochloride; HMPA for hexamethylphosphoramide; MTBE for methyl tert-butyl ether; TEA for triethylamine; TFA for trifluoroacetic acid; THF for tetrahydrofuran; and TBAB for tetrabutylammonium bromide.

The compounds and processes of the present invention will be better understood in connection with the following synthetic schemes which illustrate the methods by which the compounds of the invention can be prepared. The compounds defined above can be prepared by a variety of synthetic routes. Representative procedures are shown below in Schemes 1–14. The groups $R^1$, $R^2$, $R^3$, $R^4$, $R^5$, $R^6$, $R^7$, and $R^8$ are defined above, and groups $X^1$, $X^2$, $X^3$, and $X^4$ are defined below. It will be readily apparent to one of ordinary skill in the art that the compounds defined above can be synthesized by substitution of the appropriate reactants and agents in the syntheses shown below. It will also be apparent to one skilled in the art that the selective protection and deprotection steps, as well as the order of the steps themselves, can be carried out in varying order, depending on the nature of $R^1$, $R^2$, $R^3$, $R^4$, $R^5$, $R^6$, $R^7$, and $R^8$, to successfully complete the syntheses of compounds defined above. A thorough discussion of protecting groups is provided in Greene and Wuts, *Protective Groups in Organic Synthesis*, 2nd ed., John Wiley & Son, Inc., 1991, the relevant portions of which are incorporated herein by reference.

The groups $R^1$, $R^{13}$, $R^6$, $R^7$, $R^4$ and $R^5$ together, and $R^5$ and $R^6$ together, when each is other than hydrogen, can be introduced to the erythronolide ring (for $R^1$, $R^{13}$, $R^6$, $R^4$ and $R^5$ together, and $R^5$ and $R^6$ together) or cladinose ring (for $R^7$) from precursor compounds $R^1$—$X^1$, $R^{13}$—$X^1$, $R^6$—$X^1$, $X^1$—$(CH_2)_x$—$X^1$ or $X^1$—$C(O)$—$X^1$, and $R^7$—$X^1$, respectively. In each case, $X^1$ is an attachment group comprising a halo or sulfonate leaving group or a carbonyl activating group. The precursor compounds are commercially available or can be prepared from commercially available starting materials. For example, compounds containing an alcohol group can be elaborated to alkyl, alkenyl, alkynyl, aldehyde, ether, acid halide, ester, amide, amine, oxime, thioalkoxide, sulfinyl, sulfonyl, or carboxylic acid-containing groups by means well known in the art. Many of these groups can be further elaborated to other groups such as carbonates, carbamates, or ureas. Functional group transformations useful for preparing precursor compounds $R^1$—$X^1$, $R^{13}$—$X^1$, $R^6$—$X^1$, $X^1$—$(CH_2)_x$—$X^1$ or $X^1$—$C(O)$—$X^1$, and $R^7$—$X^1$ are disclosed in Larock, "Comprehensive Organic Transformations. A Guide to Functional Group Preparations," VCH Publishers, New York (1989), the relevant portions of which are incorporated herein by reference. The introduction of these groups to the erythronolide or cladinose ring is discussed in the schemes.

Compounds of formula (1) in Scheme 1 can be prepared from erythromycin A. The synthesis is described in U.S. Pat. Nos. 4,990,602, 4,331,803, and 4,670,549, the relevant portions of which are incorporated herein by reference. The C-9-carbonyl of erythromycin A can be protected as an oxime. Preferred protecting groups of the C-9-carbonyl are =N—O—$R^x$ or =N—O—C($R^y$)($R^z$)(O$R^x$), wherein $R^x$ is (a) —$C_1$–$C_{12}$-alkyl, (b) —$C_1$–$C_{12}$-alkyl substituted with aryl, (c) —$C_1$–$C_{12}$-alkyl substituted with substituted aryl, (d) —$C_1$–$C_{12}$-alkyl substituted with heteroaryl, (e) —$C_1$–$C_{12}$-alkyl substituted with substituted heteroaryl, (f) —$C_3$–$C_{12}$-cycloalkyl, or (g) —Si($R^a$)$_3$, wherein $R^a$ is —$C_1$–$C_{12}$-alkyl or aryl, and wherein $R^y$ and $R^z$ are independently (a) hydrogen, (b) —$C_1$–$C_{12}$-alkyl, (c) —$C_1$–$C_{12}$-alkyl substituted with aryl, or (d) —$C_1$–$C_{12}$-alkyl substituted with substituted aryl, or $R^y$ and $R^z$ taken together with the carbon to which they are attached form a —$C_3$–$C_{12}$-cycloalkyl ring. A particularly preferred carbonyl protecting group for the C-9-carbonyl of erythromycin A is O-(1-isopropoxycyclohexyl) oxime, wherein $R^y$ and $R^z$ together are cyclohexyl and $R^x$ is isopropyl.

Scheme 1

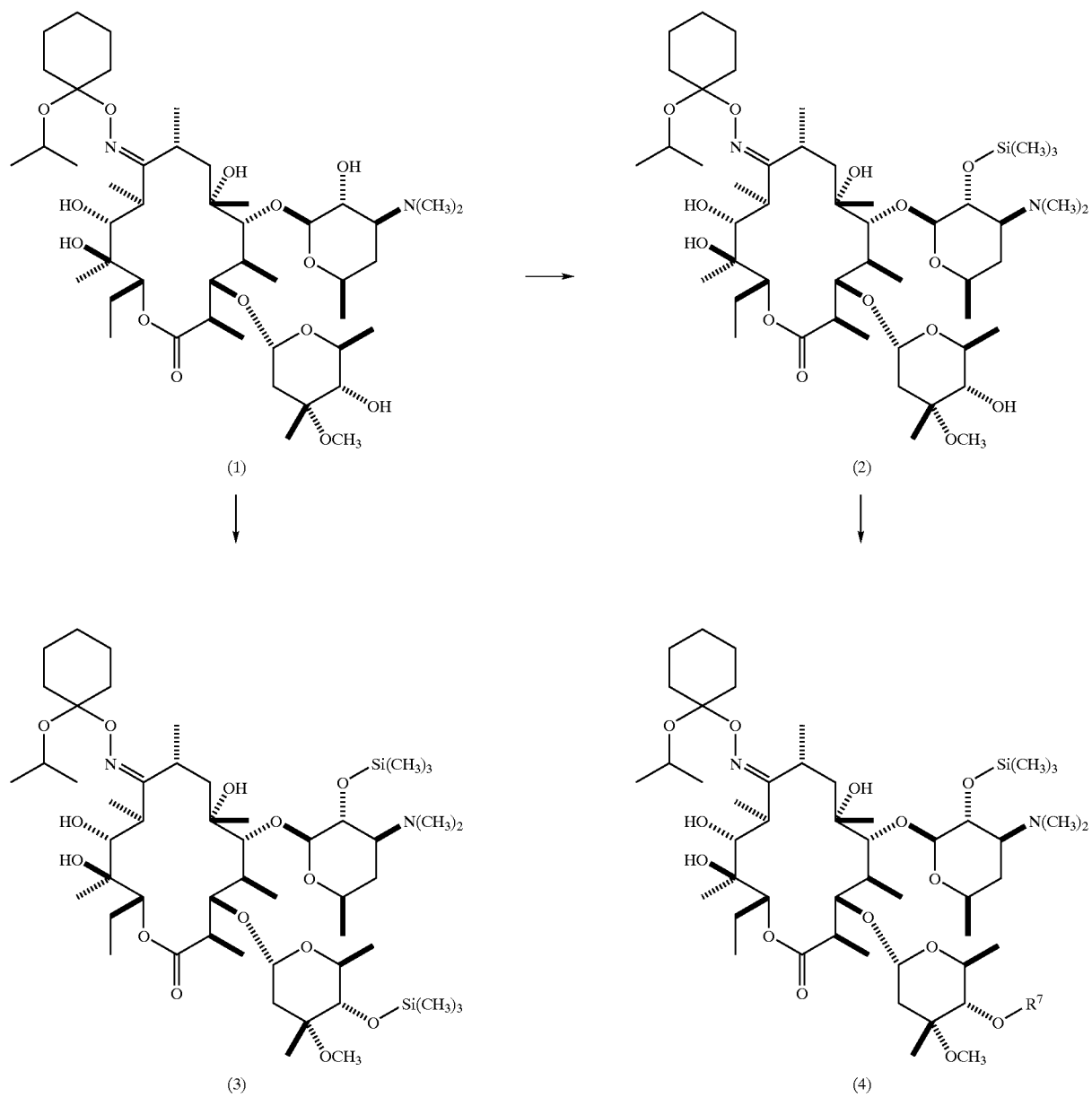

As shown in Scheme 1, the 2'-hydroxy of the desosamine ring and 4''-hydroxy of the cladinose ring of compounds of formula (1) can be protected sequentially or simultaneously by treatment of the same with hydroxy protecting group precursors to provide compounds of formulas (2) or (3), respectively. Hydroxy protecting group precursors include, acetic anhydride, benzoic anhydride, hexamethyldisilazane, a trialkylsilyl or triarylsilyl halide, or benzyl chloroformate under controlled conditions to preclude demethylation of the cladinose dimethylamine group. Preferred protecting groups include acetyl, benzoyl, and trimethylsilyl. A particularly preferred protecting group precursor is trimethylsilyl chloride. Compounds of formula (2) can be further elaborated to compounds of formula (4) by treatment of the former with $R^7$—$X^1$, wherein $X^1$ is halide, and base. When derivatizing compounds of formula (1), acid can be liberated with the progress of the reaction. For this reason, the reactions described in Scheme 1 are usually run with at least a stoichiometric amount of base present. Examples of such bases include pyridine, diisopropylethylamine, and TEA. Although the solvent used in the reaction is not particularly limited, a solvent which is not reactive with the starting materials and in which the starting materials are both soluble is generally used. Examples of such solvents include acetone, acetonitrile, diethyl ether, DCM, chloroform, ethyl acetate, THF, dioxane, or mixtures thereof. Other factors determine the product disposition, as well. For example, treatment of compounds of formula (1) with one equivalent of a hydroxy protecting group precursor and base at room temperature usually results in compounds of formula (2). Treatment of compounds of formula (1) with two equivalents of a hydroxy protecting group precursor and base with catalytic DMAP at room temperature or elevated temperature usually results in compounds of formula (3). The reaction time is generally 30 minutes to 18 hours and can be selected depending on the desired product disposition.

Scheme 2

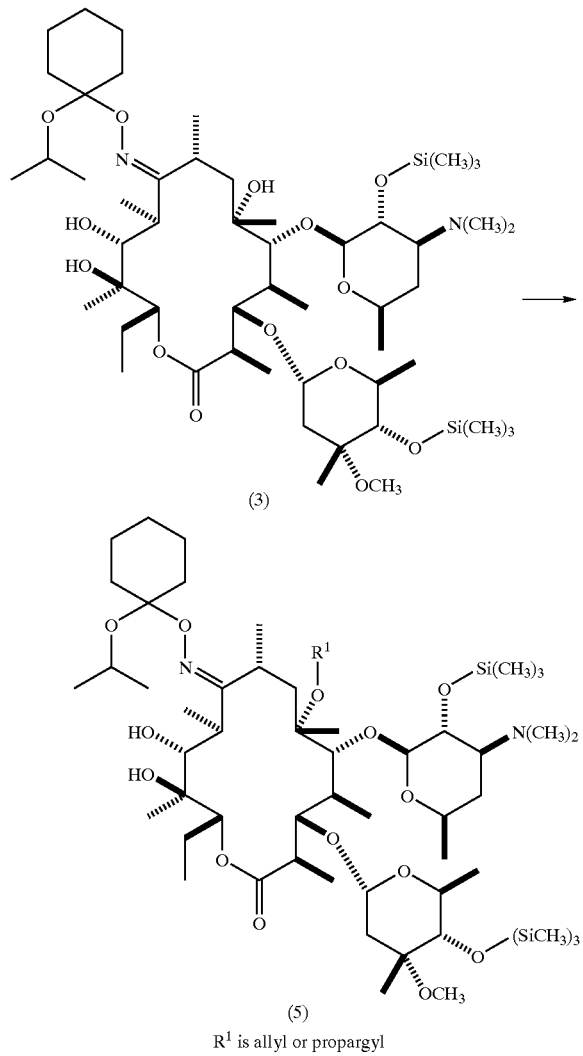

(3)

(5)

R¹ is allyl or propargyl

The conversion of compounds of formula (3) to compounds of formula (5) is shown in Scheme 2. Alkylation of compounds of formula (3) can be accomplished by treatment of the former with $R^1$—$X^1$ in the presence of base as described in U.S. Pat. No. 5,866,549, the relevant portions of which are incorporated herein by reference, and in the experimentals below. An alternative preparation of compounds of formula (I), wherein $R^1$ is allyl (—$C_3$-alkenyl), is treatment of compounds of formula (I) with $R^1$—$X^2$, wherein $R^1$ is allyl (—$C_3$-alkenyl) or a substituted alkyl and $X^2$ is a tert-butyl carbonate moiety, in the presence of a catalyst such as $Pd_2(dba)_3$, as described in commonly owned pending U.S. application Ser. No. 09/624,849, filed Jun. 24, 1999 and in Example 1, Step 1(c). Although the solvent used in these reactions is not particularly limited, a solvent which is not reactive with the starting materials and in which the starting materials are both soluble is generally used. Examples of such solvents include diethyl ether, DME, THF, dioxane, or mixtures thereof. When employing $R^1$—$X^1$ to derivative the 6-position, acid is liberated with the progress of the reaction, so it is preferable to run the reaction in the presence of a suitable deacidifying agent.

Scheme 3

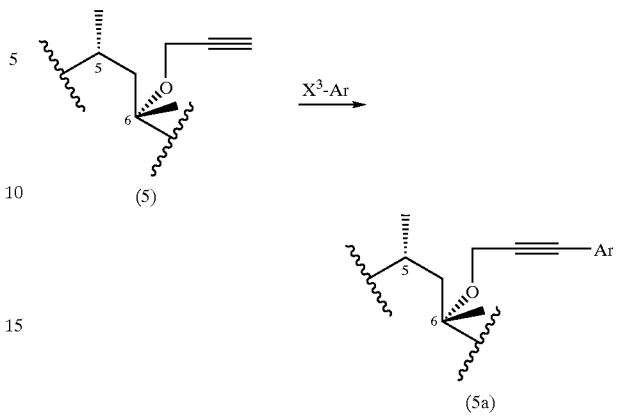

(5)

(5a)

Intraconversion compounds of the invention is also shown in Scheme 3. Compounds of formula (5), wherein $R^1$ is propargyl, can be further elaborated to compounds of formula (5a) by a number of general routes. A preferred general route is shown in Scheme 3. The 6-O propargyl group can be reacted with groups such as $X^3$—Ar wherein Ar is an unsubstituted or a substituted aryl group or heteroaryl group, respectively, and $X^3$ is one of any number of covalent bond precursors such as halides (preferably bromide and iodide) and sulfonates. The coupling reactions are performed in the presence of Pd(II) or Pd(0) catalysts with promoters such as phosphines (preferably triphenylphosphine), arsines (preferably triphenylarsine), amines (preferably pyridine and triethylamine), and inorganic bases (preferably potassium carbonate or cesium fluoride) in polar, aprotic solvents such as benzene, toluene, DMF, DMSO, DME, acetonitrile THF, or mixtures thereof at temperatures from about room temperature to about 150° C., depending on the coupling method chosen and the nature of $X^3$.

Scheme 4

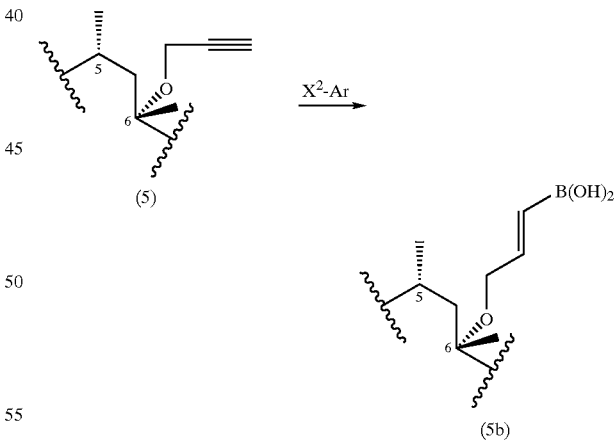

(5)

(5b)

Intraconversion compounds of the invention is also shown in Scheme 4. Compounds of formula (5), wherein $R^1$ is propargyl, can be still further elaborated intermediates of formula (5b) with borane-THF in aprotic solvents at temperatures from about −20° C. to about room temperature to provide vinyl boronic acid derivatives. Intermediates (5b) then be reacted under Suzuki conditions with $X^3$—Ar reagents, catalysts, and promoters described in Scheme 3 to provide additional compounds of formula (5). A thorough discussion of Suzuki conditions is provided in Chemical Reviews, 1995, Vol. 95, No.7, 2457–2483, the relevant portions of which are incorporated herein by reference.

Scheme 5

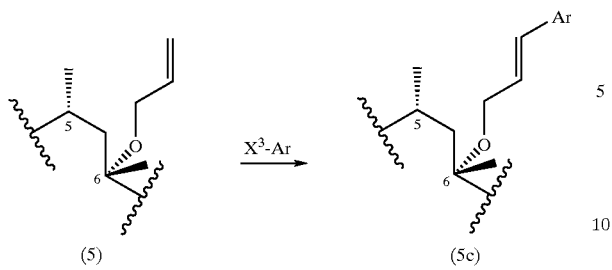

Intraconversion compounds of the invention is also shown in Scheme 5. Compounds of formula (5) can be still even further elaborated to compounds of formula (5c) by treatment with to $X^3$—Ar reagents under Heck conditions, the conditions of which are described in Larock (op. cit.) and in U.S. Pat. No. 5,866,549 (Example 1 steps 1a–g and Example 102, steps 120a–c), incorporated herein by reference.

Scheme 6

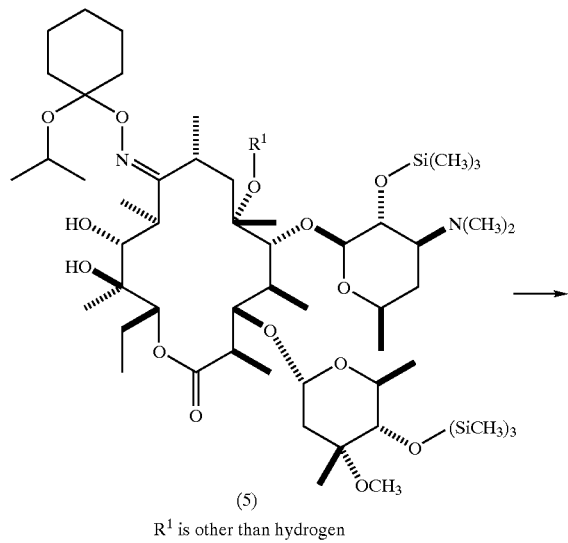

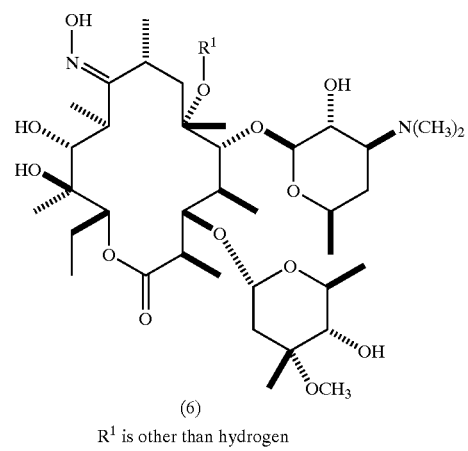

(6)
$R^1$ is other than hydrogen

As shown in Scheme 6, the conversion of compounds of formula (5) to compounds of formula (6) can be accomplished by treatment of the former with an acid such as HCl, HBr, acetic acid, or TFA. Although the solvent used in these reactions is not particularly limited, a solvent which is not reactive with the starting material and in which the starting material and the acid are both soluble is generally used. Examples of such solvents include acetonitrile, DME, THF, dioxane, or mixtures thereof. The preferred conditions for the deprotection of the 2'- and 4"-hydroxy groups of the desosamine and cladinose rings, respectively, (acetic acid in acetonitrile and water) usually result in concomitant removal of the 1-isopropoxycyclohexyl group provide the unalkylated oxime (=N—OH) at C-9.

Scheme 7

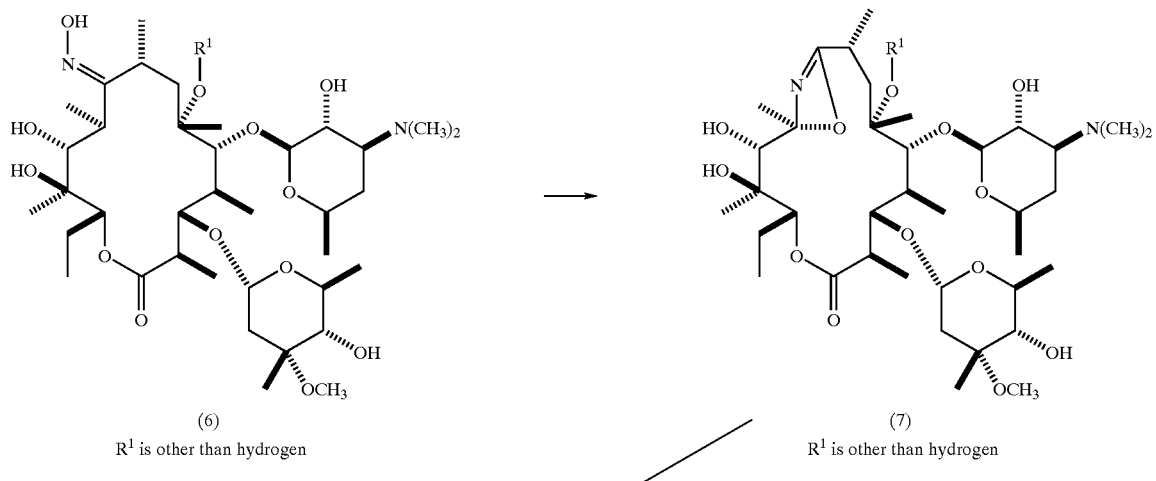

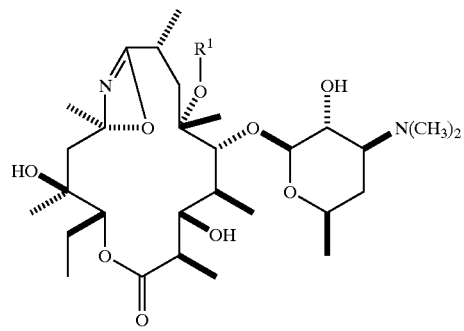

(7a)
R¹ is other than hydrogen

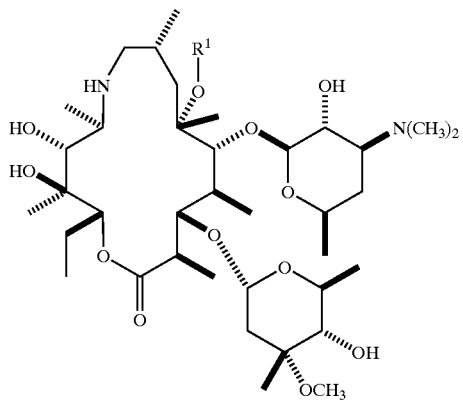

(8)
R¹ is other than hydrogen

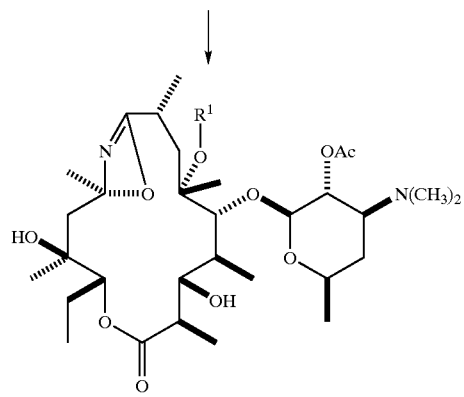

(7b)
R¹ is other than hydrogen

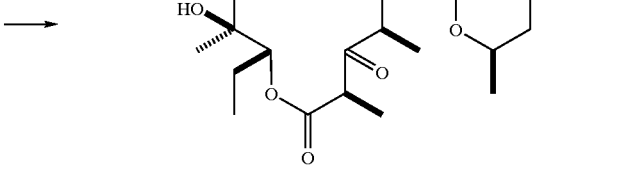

(7c)
R¹ is other than hydrogen

Synthesis of compounds of formula (III), intraconversion of compounds of formula (III) to compounds of formula (IV) and the conversion of compounds of formula (III) to compounds of formula (I) is shown in Scheme 7. Compounds of formula (6) can be treated with oxime activating agents to provide compounds of formula (7). Especially preferred oxime activating agents are sulfonyl halides such as para-toluenesulfonyl chloride, methanesulfonyl chloride, para-bromosulfonyl chloride, and para-bromosulfonyl chloride. When using sulfonyl halides to activate oximes, acid is liberated with the progress of the reaction, so it is preferable to run the reaction in the presence of a suitable deacidifying agent. For this reason, the reaction is run with at least a stoichiometric amount of base present. Examples of such bases include pyridine, diisopropylethylamine, TEA, NaHCO₃, Na₂CO₃, KHCO₃, and K₂CO₃. Conversion of compounds of formula (7) to compounds of formula (8) can be achieved by treatment of the former with reducing agents such as PtO₂, borane in tetrahydrofuran, borane dimethylsulfide, sodium cyanoborohydride, or sodium borohydride optionally in the presence of an acid such as TiCl₄, CoCl₂, AlCl₃, methanesulfonic acid, or acetic acid. In a particularly preferred embodiment, compounds of formula (6) are treated with para-toluenesulfonyl chloride and pyridine in THF to provide compounds of formula (7) which are treated with NaBH₃CN and acetic acid to provide compounds of compounds of formula (8). Although the solvent used in these reactions is not particularly limited, a solvent which is not reactive with the starting materials and in which the starting materials are both soluble is generally used. Examples of such solvents include acetone, water, acetonitrile, diethyl ether, DME, DCM, chloroform, DMF, DMA, ethyl acetate, THF, dioxane, N-methylpyrrolidinone, DMSO, diethylsulfoxide, HMPA, or mixtures thereof. The reactions generally proceed at room temperature but can be run at lower temperatures. The reaction time is generally 30 minutes to 18 hours and can be selected depending on the types of starting materials and reaction temperature.

Alternatively, compounds of formula (7) can be converted to compounds of formula (7a) by hydrolysis with dilute aqueous acid or by enzymatic hydrolysis of the former to remove the cladinose moiety from the 3-hydroxy cladinose group. Representative acids include hydrochloric acid, sulfuric acid, perchloric acid, chloroacetic acid, dichloroacetic acid, or TFA. Although the solvent used in the reaction is not particularly limited, a solvent which is not reactive with the starting materials and in which the starting materials are both soluble is generally used. Examples of such solvents include acetone, acetonitrile, C₁–C₄-alcohols, THF, dioxane, or mixtures thereof. The preferred reaction temperature is about –10° C. to about 60° C. and depends on the method chosen. Reaction times are typically about 0.5 to about 24 hours.

Compounds of formula (7a) can be converted to compounds of formula (7c) by treatment of the former with a 2′-hydroxyl protecting group to provide compounds of formula (7b) followed by oxidation of the 3-hydroxy group to a 3-oxo group using a Corey-Kim reaction with N-chlorosuccinimide-dimethyl sulfide, a Moffat oxidation with a carbodiimide-DMSO complex in the presence of pyridinium trifluoroacetate, or Dess-Martin periodinane. In a preferred embodiment, compounds of formula (7b) are added to a preformed N-chlorosuccinimide-dimethyl sulfide complex in a chlorinated solvent such as DCM or chloroform at about −10° C. to about 25° C. After stirring for about 0.5 to about 4 hours, a tertiary amine such as TEA or diisopropylethylamine is added to produce compounds of formula (7c).

Scheme 8

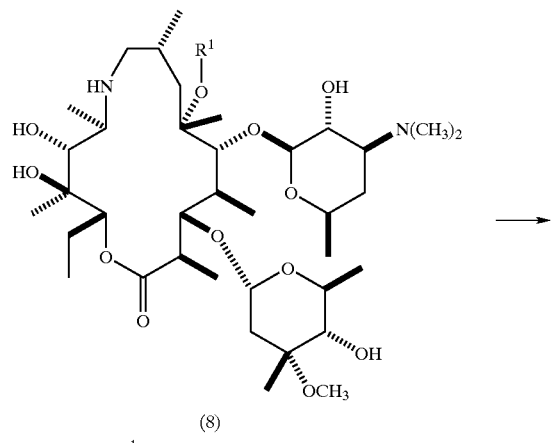

(8)
R¹ is other than hydrogen

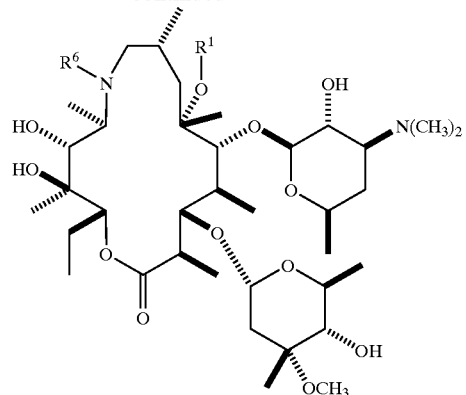

(9)
R¹ and R⁶ are other than hydrogen

Intraconversion of compounds of formula (I) are shown in Scheme 8. Compounds of formula (8) can be converted to compounds of formula (9) by treatment of the former with alkylating agent R⁶—X¹, wherein X¹ is a halo leaving group, in the presence of base. An alternative means of converting compounds of formula (8) to compounds of formula (9) is treatment of the former with alkylating agent R⁶—X⁴, wherein X⁴ is a carboxaldehyde group, in the presence of formic acid. Although the solvent used in the reaction is not particularly limited, a solvent which is not reactive with the starting materials and in which the starting materials are both soluble is generally used. Examples of such solvents include acetone, acetonitrile, diethyl ether, DCM, chloroform, ethyl acetate, THF, dioxane, or mixtures thereof. The reaction generally proceeds at elevated temperatures but can be run at lower temperatures. The reaction time is generally 30 minutes to 18 hours and can be selected depending on the types of starting materials and reaction temperature. In a particularly preferred embodiment, R⁶—X³ is reacted with (8) in chloroform at elevated temperatures.

Scheme 9

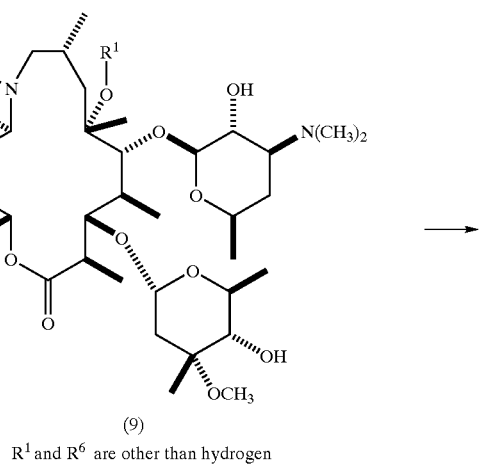

(9)
R¹ and R⁶ are other than hydrogen

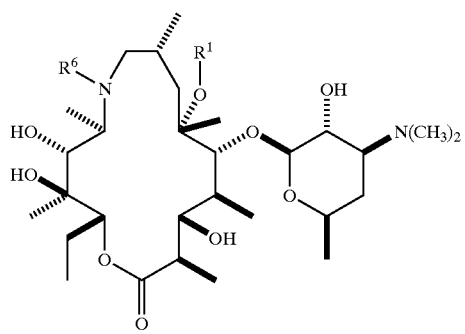

(10)
R¹ and R⁶ are other than hydrogen

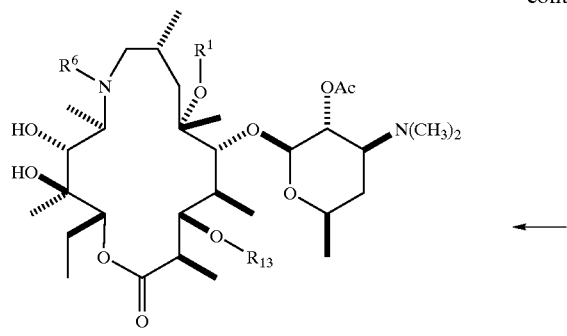

(12)
R$^1$, R$^6$, and R$^{13}$ are other than hydrogen

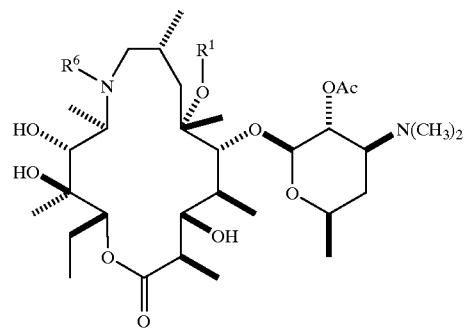

(11)
R$^1$ and R$^6$ are other than hydrogen

Conversion of compounds of formula (I) to compounds of formula (II) and intraconversion compounds of formula (II) are shown in Scheme 9. Compounds of formula (9) can be converted to compounds of formula (10) by hydrolysis with dilute aqueous acid or by enzymatic hydrolysis to remove the cladinose moiety from the 3-hydroxy cladinose group. Representative acids include hydrochloric acid, sulfuric acid, perchloric acid, chloroacetic acid, dichloroacetic acid, or TFA. Although the solvent used in the reaction is not particularly limited, a solvent which is not reactive with the starting materials and in which the starting materials are both soluble is generally used. Examples of such solvents include acetone, acetonitrile, C$_1$–C$_4$-alcohols, THF, dioxane, or mixtures thereof. The preferred reaction temperature is about –10° C. to about 60° C. and depends on the method chosen. Reaction times are typically about 0.5 to about 24 hours. Compounds of formula (10) can then be converted to compounds of formula (11) by the hydroxyl protection described for compounds of formula (1) in Scheme 1. Conversion of compounds of formula (11) to compounds of formula(12) can be achieved by treatment of the former with R$^{13}$—X$^1$, wherein X$^1$ is an carbonyl-activating group.

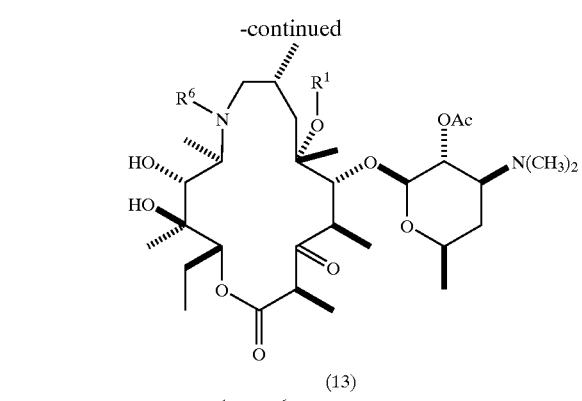

(13)
R$^1$ and R$^6$ are other than hydrogen

Intraconversion compounds of formula (II) is shown in Scheme 10. Conversion of compounds of formula (12) to compounds of formula (13) can be accomplished by oxidation of the 3-hydroxy group to a 3-oxo group using a Corey-Kim reaction with N-chlorosuccinimide-dimethyl sulfide, a Moffat oxidation with a carbodiimide-DMSO complex in the presence of pyridinium trifluoroacetate, or Dess-Martin periodinane. In a preferred embodiment, compounds of formula (12) are added to a preformed N-chlorosuccinimide-dimethyl sulfide complex in a chlorinated solvent such as DCM or chloroform at about –10° C. to about 25° C. After stirring for about 0.5 to about 4 hours, a tertiary amine such as TEA or diisopropylethylamine is added to produce compounds of formula (13).

Scheme 10

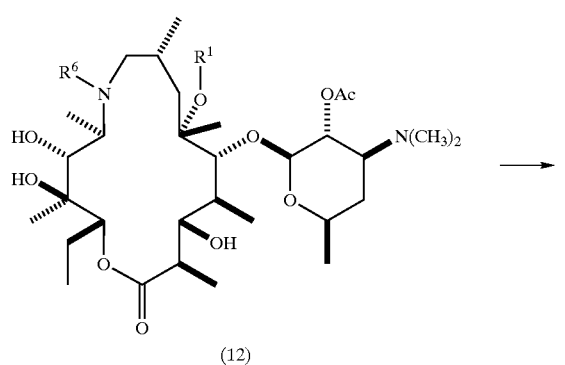

(12)
R$^1$ and R$^6$ are other than hydrogen

Scheme 11

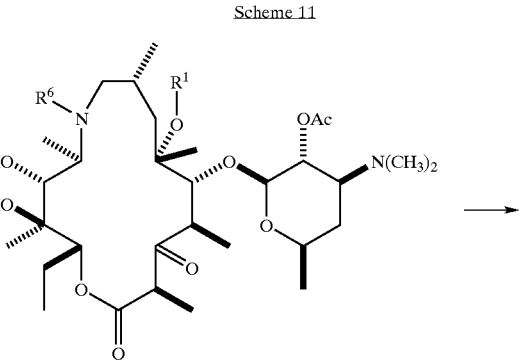

(13)
R$^1$ and R$^6$ are other than hydrogen

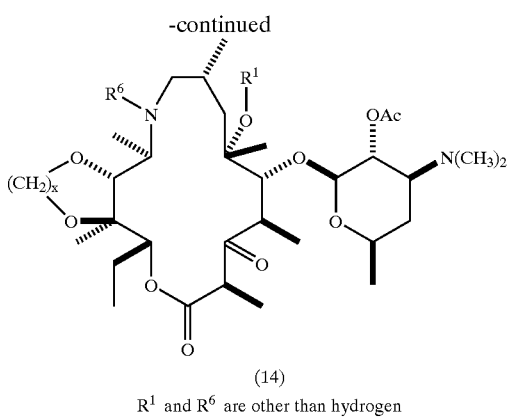

(14)

R[1] and R[6] are other than hydrogen

Intraconversion compounds of formula (II) is also shown in Scheme 11. Conversion of compounds of formula (13) to compounds of formula (14) can be achieved by treatment of the former with a bifunctional alkylating agent such as $X^1$—$(CH_2)_x$—$X^1$, wherein $X^1$ is a halo leaving group, in the presence of base, using the same conditions as described for the introduction of $R^1$ to compounds of formula (3) in Scheme 2.

Scheme 12

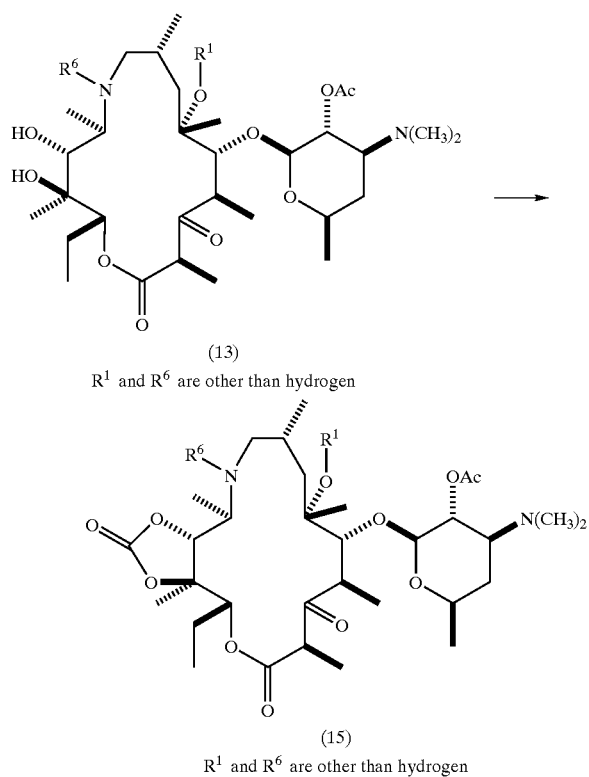

(13)

R[1] and R[6] are other than hydrogen (15)

R[1] and R[6] are other than hydrogen

Intraconversion compounds of formula (II) is also shown in Scheme 12. Conversion of compounds of formula (13) to compounds of formula (15) can be achieved by treatment of the former with a carbonyl-activating group such as CDI, phosgene or triphosgene in the presence of base. When using phosgene or trophosgene to derivative compounds of formula (13), acid is liberated with the progress of the reaction, so it is preferable to run the reaction in the presence of a suitable deacidifying agent. For this reason, the reaction is run with at least a stoichiometric amount of base present.

Examples of such bases include pyridine, diisopropylethylamine, TEA, $NaHCO_3$, $Na_2CO_3$, $KHCO_3$, and $K_2CO_3$. Although the solvent used in these reactions is not particularly limited, a solvent which is not reactive with the starting materials and in which the starting materials are both soluble is generally used. Examples of such solvents include acetone, acetonitrile, DME, DCM, chloroform, DMF, DMA, ethyl acetate, THF, dioxane, benzene, toluene, or mixtures thereof. The reactions generally proceed at lower temperatures but can be run at higher temperature. The reaction time is generally 30 minutes to 18 hours and can be selected depending on the types of starting materials and reaction temperature.

Scheme 13

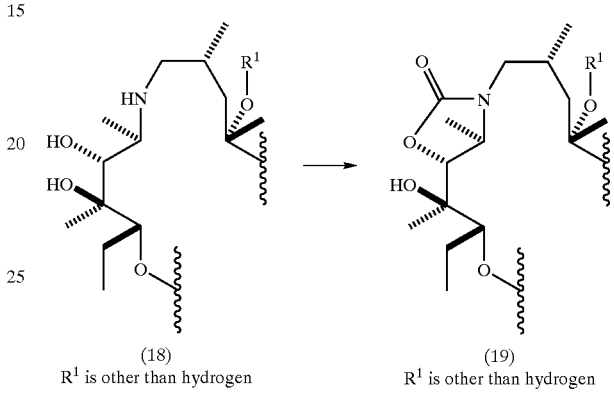

(18)  (19)
R[1] is other than hydrogen    R[1] is other than hydrogen

Intraconversion compounds of the invention is also shown in Scheme 13. Compounds of formula (18) can be treated with carbonyl activating groups as described for compounds of formula (13) in Scheme 12 to provide compounds of formula (19).

Scheme 14

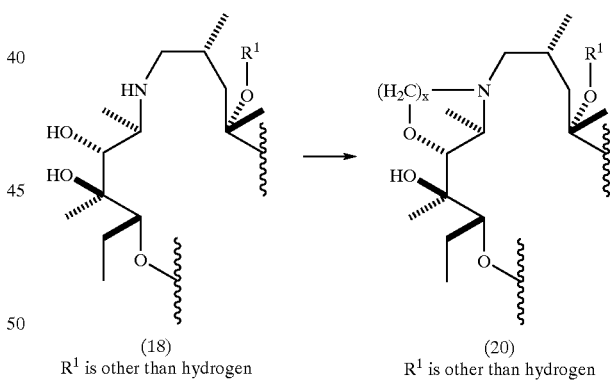

(18)  (20)
R[1] is other than hydrogen    R[1] is other than hydrogen

Intraconversion compounds of the invention is also shown in Scheme 13. Compounds of formula (18) can be treated with a $X^1$—$(CH_2)_x$—$X^1$ as described for compounds of formula (13) in Scheme 11 to provide compounds of formula (20).

The compounds and processes of the present invention will be better understood in connection with the following examples, which are intended as an illustration of and not a limitation upon the scope of the invention.

Clarithromycin (3-O-cladinosyl-5-O-desosaminyl-6-O-methyl-erythronolide A) was obtained from Abbott Laboratories. All other starting materials not mentioned specifically by example were purchased from Aldrich Chemical Company (Milwaukee, Wis.).

EXAMPLE 1

Compound of formula (III): $R^1$ is —$CH_2CH=CH_2$, $R^4$ is hydrogen, $R^7$ is hydrogen, $R^8$ is hydrogen Step 1a: Compound (1) from Scheme 1

The desired product was prepared as described in U.S. Pat. No. 4,990,602, Examples (1) and (2), and substituting 1-cyclohexen-1-yl isopropyl ether for 2-methoxypropene.

Step 1b: allyl tert-butyl carbonate

The desired product was prepared as described in the Canadian Journal of Chemistry, 1985, Vol.63, pp.153–162.

Step 1c: Compound (5) from Scheme 2: $R^1$ is —$CH_2CH=CH_2$, $R^4$ is hydrogen, $R^5$ is hydrogen, $R^7$ is —$Si(CH_3)_3$, $R^8$ is —$Si(CH_3)_3$, $R^x$ is iso-propyl, $R^y$ and $R^z$ together are cyclohexyl A mixture of $Pd_2(dba)_3$ (0.120 g, 0.131 mmol) and dppb (111 mg, 0.259 mmol) was treated with the product from Step 1a (azeotropically dried with toluene, 25.0 g, 24.23 mmol) and the product from Step 1b (4.6 g, 29.1 mmol) in THF (100 mL), heated to reflux for 30 minutes, cooled, and concentrated. The concentrate was dissolved in ethyl acetate (250 mL), and the resulting solution was washed with half-saturated $Na_2CO_3$ and brine, dried ($Na_2SO_4$), filtered, and concentrated to provide 25.2 g of the desired product of sufficient purity for use without further purification.

MS ($DCI/NH_3$) m/z 1073 $(M+H)^+$.

Step 1d: Compound (6) from Scheme 6: $R^1$ is —$CH_2CH=CH_2$, $R^4$ is hydrogen, $R^5$ is hydrogen, $R^7$ is hydrogen, $R^8$ is hydrogen, $R^x$ is hydrogen A suspension of the product from Step 1c (25.2 g, 23.5 mmol) in acetonitrile (240 mL) and water (50 mL) was treated with glacial acetic acid (70 mL), and the resulting solution was stirred at room temperature for 3 days and concentrated. The concentrate was dissolved in DCM (100 mL), and the resulting solution was washed sequentially with half-saturated $Na_2CO_3$ (until the pH of the wash was 10), water, and brine, dried ($Na_2SO_4$), filtered, and concentrated to provide 17.4 g of the desired product of sufficient purity for use without further purification.

MS ($DCI/NH_3$) m/z 790 $(M+H)^+$.

Step 1e: Compound of formula (III): $R^1$ is —$CH_2CH=CH_2$, $R^4$ is hydrogen, $R^7$ is hydrogen, $R^8$ is hydrogen A solution of the product from Step 1d (7.0 g, 8.88 mmol) in pyridine (90 mL) at 0° C. was treated over 30 minutes with a solution of para-toluenesulfonyl chloride (3.39 g, 17.77 mmol) in THF (90 mL), stirred for 2.5 hours, heated to 40° C. for 20 hours, cooled, and treated with ethyl acetate (200 mL). The resulting solution was washed sequentially with half-saturated $Na_2CO_3$, water, and brine, dried ($Na_2SO_4$), filtered, and concentrated. The concentrate was purified by flash column chromatography on silica gel with 96:4 acetone/TEA to provide 2.86 g of the desired product.

MS ($DCI/NH_3$) m/z 771 $(M+H)^+$.

EXAMPLE 2

Compound of formula (I): $R^1$ is —$CH_2CH=CH_2$, $R^4$ is hydrogen, $R^5$ is hydrogen, $R^6$ is hydrogen, $R^7$ is hydrogen, $R^8$ is hydrogen A solution of Example 1 (100 mg, 0.13 mmol) and one crystal of bromocresol green in methanol (1 mL) at room temperature was treated with glacial acetic acid until the color of the solution changed from blue to yellow, treated a first time with $NaBH_3CN$ (16 mg, 0.26 mmol), stirred at room temperature for 18 hours, treated a second time with $NaBH_3CN$ (16 mg, 0.260 mmol), stirred for 4 hours, treated a third time with $NaBH_3CN$ (32 mg, 0.52 mmol), stirred for 3 hours, and treated a fourth time with $NaBH_3CN$ (32 mg, 0.52 mmol), and stirred for 16 hours, treated with 1M NaOH (5 mL), and extracted with MTBE. The extract was washed with brine, dried ($Na_2SO_4$), filtered, and concentrated. The concentrate was purified by flash column chromatography on silica gel with 9:1:0.5 DCM/methanol/concentrated $NH_4OH$ to provide 15.1 mg of the desired product.

MS ($DCI/NH_3$) m/z 775 $(M+H)^+$.

EXAMPLE 3

Compound of formula (I): $R^1$ is —$CH_2CH=CH_2$, $R^4$ is hydrogen, $R^5$ is hydrogen, $R^6$ is methyl, $R^7$ is hydrogen, $R^8$ is hydrogen A solution of Example 2 (840 mg, 1.09 mmol) in chloroform (20 mL) at room temperature was treated dropwise with a mixture of formic acid (90 µL, 2.39 mmol) and 37% aqueous formaldehyde (196 µL, 7.05 mmol), heated to reflux for 15 hours, cooled, and treated with half-saturated $Na_2CO_3$ (50 mL). The layers were separated and the aqueous layer was extracted with chloroform. The extract was washed with water and brine, dried ($Na_2SO_4$), filtered and concentrated to provide 1.0 g of the desired product of sufficient purity for use without further purification.

MS ($DCI/NH_3$) m/z 789 $(M+H)^+$.

EXAMPLE 4

Compound of formula (II): $R^1$ is —$CH_2CH=CH_2$, $R^2$ is hydrogen, $R^3$ is —$OR^{13}$, $R^{13}$ is hydrogen, $R^4$ is hydrogen, $R^5$ is hydrogen, $R^6$ is methyl, $R^8$ is hydrogen A solution of Example 3 (757 mg, 0.972 mmol) in 90% ethanol (15 mL) was treated with water (30 mL), treated with 1M HCl (4.86 mL, 4.86 mmol), stirred at room temperature for 15.5 hours, and concentrated. The concentrate was dissolved in water (50 mL), and the resulting solution was washed with MTBE, made basic (pH 10) with half-saturated $Na_2CO_3$, and extracted with isopropyl acetate. The extract was washed with brine (50 mL), dried ($Na_2SO_4$), filtered, and concentrated to provide 637 mg of the desired product of sufficient purity for use without further purification.

MS ($DCI/NH_3$) m/z 631 $(M+H)^+$.

EXAMPLE 5

Compound of formula (II): $R^1$ is —$CH_2CH=CH$-(3-quinolinyl), $R^2$ and $R^3$ together are oxo, $R^4$ is hydrogen, $R^5$ is hydrogen, $R^6$ is methyl, $R^8$ is hydrogen Step 5a: Compound (12) in Scheme 10: $R^1$ is —$CH_2CH=CH_2$, $R^2$ is hydrogen, $R^3$ is —$OR^{13}$, $R^{13}$ is hydrogen, $R^4$ is hydrogen, $R^5$ is hydrogen, $R^6$ is methyl, $R^8$ is —$C(O)CH_3$ A solution of Example 4 (590 mg, 0.937 mmol) in DCM (12 mL) at room temperature was treated sequentially with TEA (196 µL, 1.41 mmol) and acetic anhydride (133 µL, 1.41 mmol), stirred for 20 hours, diluted with DCM (25 mL), washed with saturated $NaHCO_3$ and brine (25 mL), dried ($Na_2SO_4$), filtered, and concentrated to provide 654 mg of the desired product of sufficient purity for use without further purification.

MS ($DCI/NH_3$) m/z 673 $(M+H)^+$.

Step 5b: (Option 1): Compound (13) in Scheme 11: $R^1$ is —$CH_2CH=CH_2$, $R^2$ is hydrogen, $R^3$ and $R^4$ together are oxo, $R^4$ is hydrogen, $R^5$ is hydrogen, $R^6$ is methyl, $R^8$ is —$C(O)CH_3$ A solution of the product from Step 5a (25 mg, 0.037 mmol) in DCM (12 mL) at room temperature was treated sequentially with DMSO (73 μL, 1.02 mmol) and EDCI (57 mg, 0.29 mmol), stirred for 30 minutes, treated with pyridinium trifluoroacetate (58 mg, 0.29 mmol), stirred at room temperature for 44 hours, treated with water (10 mL), and extracted with DCM. The extract was washed with saturated NaHCO$_3$ and brine, dried (Na$_2$SO$_4$), filtered, and concentrated to provide 21.8 mg of the desired product of sufficient purity for use without further purification.

MS (DCI/NH$_3$) m/z 671 (M+H)$^+$.

Step 5b (Option 2): Compound (13) in Scheme 11: R$^1$ is —CH$_2$CH=CH$_2$, R$^2$ is hydrogen, R$^3$ and R$^4$ together are oxo, R$^4$ is hydrogen, R$^5$ is hydrogen, R$^6$ is methyl, R$^8$ is —C(O)CH$_3$ A solution of the product from Step 5a (200 mg, 0.298 mmol) in DCM (3 mL) at 0° C. was treated with Dess-Martin periodinane (139 mg, 0.33 mmol), stirred for 30 minutes, warmed to room temperature, stirred for 2.5 hours, treated with half-saturated Na$_2$CO$_3$ (25 mL), and extracted with DCM. The extract was washed with half-saturated Na$_2$CO$_3$ and brine, dried (Na$_2$SO$_4$), filtered, and concentrated. The concentrate was purified by flash chromatography on silica gel with 99:1:1 DCM/methanol/concentrated NH$_4$OH to provide 51 mg of the desired product.

MS (DCI/NH$_3$) m/z 671 (M+H)$^+$.

Step 5c: Compound (13) in Scheme 11: R$^1$ is —CH$_2$CH=CH-(3-quinolinyl), R$^2$ is hydrogen, R$^3$ and R$^4$ together are oxo, R$^4$ is hydrogen, R$^5$ is hydrogen, R$^6$ is methyl, R$^8$ is —C(O)CH$_3$ A mixture of the product from Step 5b, (133 mg, 0.167 mmol) 3-bromoquinoline (42 μL, 312 mmol), TBAB (76 mg, 0.327 mmol), diisopropylethylamine (103 μL, 0.592 mmol), and palladium (II) acetate (33 mg, 0.147 mmol) in DME (5 mL) in a sealed tube was heated at 80° C. for 16 hours, cooled to room temperature, treated with half-saturated Na$_2$CO$_3$ (15 mL), and extracted with ethyl acetate. The extract was washed sequentially with half-saturated Na$_2$CO$_3$, water, and brine, dried (Na$_2$SO$_4$), filtered, and concentrated. The concentrate was purified by flash column chromatography on silica gel with 99:1:1 DCM/methanol/concentrated NH$_4$OH to provide 58.6 mg of the desired product.

MS (DCI/NH$_3$) m/z 798 (M+H)$^+$.

Step 5d: Compound of formula (II): R$^1$ is —CH$_2$CH=CH-(3-quinolinyl), R$^2$ and R$^3$ together are oxo, R$^4$ is hydrogen, R$^5$ is hydrogen, R$^6$ is methyl, R$^8$ is hydrogen A solution of the product from Step 5c (70 mg, 0.088 mmol) in methanol (5 mL) was stirred at room temperature for 40 hours and concentrated. The concentrate was purified by flash column chromatography on silica gel with 98:2:1 DCM/methanol/concentrated NH$_4$OH to provide 15 mg of the desired product.

MS (DCI/NH$_3$) m/z 756 (M+H)$^+$.

EXAMPLE 6

Compound of formula (II): R$^1$ is —CH$_2$CH=CH-(3-quinolinyl), R$^2$ and R$^3$ together are oxo, R$^4$ and R$^5$ together are —C(O)—, R$^6$ is methyl, R$^8$ is hydrogen Step 6a: Compound (15) from Scheme 12: R$^1$ is —CH$_2$CH=CH-(3-quinolinyl), R$^2$ and R$^3$ together are oxo, R$^4$ and R$^5$ together are —C(O)—, R$^6$ is methyl, R$^8$ is —C(O)CH$_3$ A solution of the product from Step 5c (59 mg, 0.074 mmol) in DCM (1.5 mL) was treated with pyridine (28 μL, 0.221 mmol), cooled to −10° C., treated with triphosgene (218 mg, 0.074 mmol), stirred for 2 hours, treated with additional pyridine (3 drops) and triphosgene (10 mg), stirred for 21 hours, treated with ethyl acetate (15 mL) and DCM (15 mL), and washed half-saturated Na$_2$CO$_3$. The wash was extracted with DCM, and the combined extracts were washed with brine, dried (Na$_2$SO$_4$), and concentrated. The concentrate was purified by flash chromatography on silica gel with 99:1:1 DCM/methanol/concentrated NH$_4$OH to provide 34.2 mg of the desired product.

MS (DCI/NH$_3$) m/z 824 (M+H)$^+$.

Step 6b: Compound of formula (II): R$^1$ is —CH$_2$CH=CH-(3-quinolinyl), R$^2$ and R$^3$ together are oxo, R$^4$ and R$^5$ together are —C(O)—, R$^6$ is methyl, R$^8$ is hydrogen A solution of Example 12 (34 mg, 0.042 mmol) in methanol (2.5 mL) was stirred at room temperature for 20 hours and concentrated to provide 28.5 mg of the desired product of sufficient purity for use without further purification.

MS (DCI/NH$_3$) m/z 782 (M+H)$^+$.

EXAMPLE 7

Compound of formula (I): R$^1$ is —CH$_2$CH=CH-(3-quinolinyl), R$^4$ is hydrogen, R$^5$ is hydrogen, R$^6$ is methyl, R$^7$ is hydrogen, R$^8$ is hydrogen A mixture of Example 3, 3-bromoquinoline (26 μL, 0.19 mmol), tri(o-tolyl)phosphine (6 mg, 0.019 mmol), TEA (53 μL, 39 mg, 0.381mmol), and palladium (II) acetate (3 mg, 0.013 mmol) in acetonitrile (2.5 mL) in a sealed tube was heated at 60° C. for 1 hour and at 90° C. for 20 hours, cooled to room temperature, and treated with ethyl acetate (25 mL) and half-saturated Na$_2$CO$_3$ (25 mL). The layers were separated, and the aqueous layer was extracted with ethyl acetate. The extract was washed with water and brine, dried (Na$_2$SO$_4$), filtered, and concentrated. The concentrate was purified by flash column chromatography on silica gel with 9:1:0.5 DCM/methanol/concentrated NH$_4$OH to provide 25 mg of the desired product.

MS (DCI/NH$_3$) m/z 916 (M+H)$^+$.

What is claimed is:

1. A compound selected from the group consisting of compounds of formula (I)

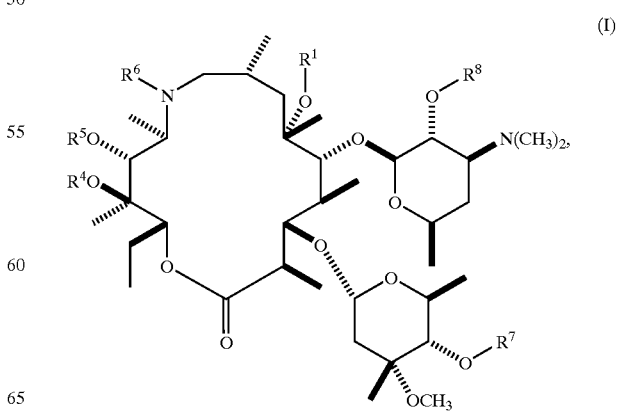

compounds of formula (II)

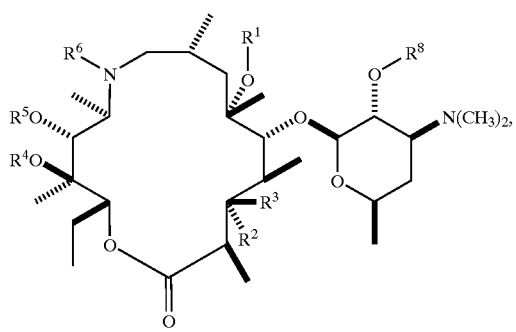

compounds of formula (III)

compounds of formula (IV)

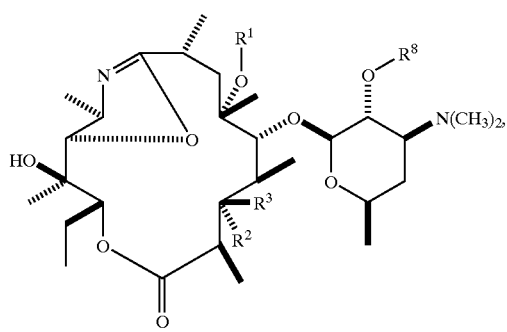

or pharmaceutically acceptable salts thereof, wherein, in formulas (I)–(IV), $R^1$ is selected from the group consisting of
(1) —$C_3$–$C_{12}$-alkenyl, and
(2) —$C_3$–$C_{12}$-alkynyl,
wherein (1)–(2) can be optionally substituted with one, two, or three substituents independently selected from the group consisting of
(a) halogen,
(b) —$OR^9$, wherein $R^9$ is selected from the group consisting of
(i) hydrogen,
(ii) —$C_1$–$C_{12}$-alkyl,
(iii) —$C_2$–$C_{12}$-heteroalkyl, wherein (ii) and (iii) can be optionally substituted with one, two, or three substituents independently selected from the group consisting of
(1') aryl,
(2') substituted aryl,
(3') heteroaryl, and
(4') substituted heteroaryl,
(iv) aryl,
(v) substituted aryl,
(vi) heteroaryl, and
(xv) substituted heteroaryl,
(c) —$NR^{11}R^{12}$, wherein $R^{11}$ and $R^{12}$ are independently selected from the group consisting of
(i) hydrogen,
(ii) —$C_1$–$C_{12}$-alkyl,
(iii) —$C_2$–$C_{12}$-heteroalkyl,
wherein (ii) and (iii) can be optionally substituted with one, two, or three substituents independently selected from the group consisting of
(1') aryl,
(2') substituted aryl,
(3') heteroaryl, and
(4') substituted heteroaryl,
(iv) aryl,
(v) substituted aryl,
(vi) heteroaryl, and
(xv) substituted heteroaryl, or
$R^{11}$ and $R^{12}$, together with the atom to which they are attached, form a heterocycloalkyl ring, wherein the heterocycloalkyl ring can be optionally substituted,
(d) =N—O—$R^9$, wherein $R^9$ is defined above,
(e) aryl,
(f) substituted aryl,
(g) heteroaryl,
(h) substituted heteroaryl,
(i) —$C_3$–$C_8$-cycloalkyl,
(j) heterocycloalkyl,
(k) substituted heterocycloalkyl,
(l) —$NHC(O)R_9$, wherein $R_9$ is defined above,
(m) —$NHC(O)OR^{10}$, wherein $R^{10}$ is selected from the group consisting of
(i) —$C_1$–$C_{12}$-alkyl,
(ii) —$C_1$–$C_{12}$-heteroalkyl,
wherein (i) and (ii) can be optionally substituted with one, two, or three substituents independently selected from the group consisting of
(1') aryl,
(2') substituted aryl,
(3') heteroaryl, and
(4') substituted heteroaryl,
(iii) aryl,
(iv) substituted aryl,
(v) heteroaryl, and
(vi) substituted heteroaryl,
(n) —$NHC(O)NR^{11}R^{12}$, wherein $R^{11}$ and $R^{12}$ are defined above,
(o) —$OC(O)R^{10}$, wherein $R^{10}$ is defined above,
(p) —$OC(O)OR^{10}$, wherein $R^{10}$ is defined above,
(q) —$OC(O)NR^{11}R^{12}$, where in $R^{11}$ and $R^{12}$ are defined above,
(s) —$CO_2R^9$, wherein $R^9$ is defined above, and
(t) —$C(O)NR^{11}R^{12}$, wherein $R^{11}$ and $R^{12}$ are defined above;

$R^2$ is hydrogen;
$R^3$ is —$OR^{13}$, wherein $R^{13}$ is selected from the group consisting of
 (1) hydrogen,
 (2) —$C(O)R^{10}$, wherein $R^{10}$ is defined above,
 (3) —$CO_2R^{10}$, wherein $R^{10}$ is defined above, and
 (4) —$C(O)NR^{11}R^{12}$, wherein $R^{11}$ and $R^{12}$ are defined above; or
$R^2$ and $R^3$ together are oxo;
$R^4$ and $R^5$ are hydrogen; or
$R^4$ and $R^5$ together are —C(O)— or —$(CH_2)_x$—, wherein x is one, two, or three; or
$R^5$ and $R^6$ together are —C(O)— or —$(CH_2)_x$—, wherein x is defined above;
$R^6$ is selected from the group consisting of
 (1) hydrogen,
 (2) —$C_1$–$C_{12}$-alkyl,
 (3) (1) —$C_3$–$C_{12}$-alkenyl,
 and
 (4) (2) —$C_3$–$C_{12}$-alkynyl,
wherein (1)–(4) can be optionally substituted with one, two, or three substituents independently selected from the group consisting of
 (a) halogen,
 (b) —$OR^9$, wherein $R^9$ is selected from the group consisting of
  (i) hydrogen,
  (ii) —$C_{1-12}$-alkyl,
  (iii) —$C_2$–$C_{12}$-heteroalkyl,
  wherein (ii) and (iii) can be optionally substituted with one, two, or three substituents independently selected from the group consisting of
   (1') aryl,
   (2') substituted aryl,
   (3') heteroaryl,
   and
   (4') substituted heteroaryl,
  (iv) aryl,
  (v) substituted aryl,
  (vi) heteroaryl, and
  (xv) substituted heteroaryl,
 (c) —$NR^{11}R^{12}$, wherein $R^{11}$ and $R^{12}$ are independently selected from the group consisting of
  (i) hydrogen,
  (ii) —$C_{1-12}$-alkyl,
  (iii) —$C_2$–$C_{12}$-heteroalkyl,
  wherein (ii) and (iii) can be optionally substituted with one, two, or three substituents independently selected from the group consisting of
   (1') aryl,
   (2') substituted aryl,
   (3') heteroaryl, and
   (4') substituted heteroaryl,
  (iv) aryl,
  (v) substituted aryl,
  (vi) heteroaryl, and
  (xv) substituted heteroaryl, or
 $R^{11}$ and $R^{12}$, together with the atom to which they are attached, form a heterocycloalkyl ring, wherein the heterocycloalkyl ring can be optionally substituted,
 (d) =N—O—$R^9$, wherein $R^9$ is defined above,
 (e) aryl,
 (f) substituted aryl,
 (g) heteroaryl,
 (h) substituted heteroaryl,
 (i) —$C_3$–$C_8$-cycloalkyl,
 (j) heterocycloalkyl,
 (k) substituted heterocycloalkyl,
 (l) —$NHC(O)R^9$, wherein $R^9$ is defined above,
 (m) —$NHC(O)OR^{10}$, wherein $R^{10}$ is selected from the group consisting of
  (i) —$C_1$–$C_{12}$-alkyl,
  (ii) —$C_1$–$C_{12}$-heteroalkyl,
  wherein (i) and (ii) can be optionally substituted with one, two, or three substituents independently selected from the group consisting of
   (1') aryl,
   (2') substituted aryl,
   (3') heteroaryl, and
   (4') substituted heteroaryl,
  (iii) aryl,
  (iv) substituted aryl,
  (v) heteroaryl, and
  (vi) substituted heteroaryl
 (n) —$NHC(O)NR^{11}R^{12}$, wherein $R^{11}$ and $R^{12}$ are defined above,
 (o) —$OC(O)R^{10}$, wherein $R^{10}$ is defined above,
 (p) —$OC(O)OR^{10}$, wherein $R^{10}$ is defined above,
 (q) —$OC(O)NR^{11}R^{12}$, wherein $R^{11}$ and $R^{12}$ are defined above,
 (r) —$C(O)R^9$, wherein $R^9$ is defined above,
 (s) —$CO_2R^9$, wherein $R^9$ is defined above, and
 (t) —$C(O)NR^{11}R^{12}$, wherein $R^{11}$ and $R^{12}$ are defined above;
$R^7$ is selected from the group consisting of
 (1) hydrogen,
 (2) —$C_1$–$C_{12}$-alkyl,
 (3) —$C_3$–$C_{12}$-alkenyl,
 (4) —$C_3$–$C_{12}$-alkynyl,
 (5) —$C_2$–$C_{12}$-heteroalkyl,
 (6) —$C_4$–$C_{12}$-heteroalkenyl,
 (7) —$C_4$–$C_{12}$-heteroalkynyl,
 wherein (2)–(7) can be optionally substituted with one, two, or three substituents independently selected from the group consisting of
  (a) halo,
  (b) hydroxy,
  (c) —$NR^{11}R^{12}$, wherein $R^{11}$ and $R^{12}$ are defined above,
  (d) aryl,
  (e) substituted aryl,
  (f) heteroaryl, and
  (g) substituted heteroaryl,
 (8) —$C(O)R^9$, wherein $R_9$ is defined above,
 (9) —$CO_2R^9$, wherein $R_9$ is defined above, and
 (11) —$C(O)NR^{11}R^{12}$, wherein $R^{11}$ and $R^{12}$ are defined above; and
$R^8$ is hydrogen or a hydroxy protecting group;
wherein substituted aryl is an aryl group substituted by independent replacement of one, two, or three of the hydrogen atoms thereon with —F, —Cl, —Br, —I, —OH, —NO$_2$, —CN, —C(O)—C$_1$-C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$-C$_6$-alkyl, —CONH-aryl, —CONH-heteroaryl, —OC(O)—C$_1$-C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$-C$_6$-alkyl, —OCONH-aryl, —OCONH-heteroaryl, —NHC(O)—C$_1$-C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$-C$_6$-alkyl, —NHCONH-aryl, —NHCONH-heteroaryl, —SO$_2$—C$_1$-C$_6$-alkyl, —SO$_2$-aryl, —SO$_2$-heteroaryl, —SO$_2$NH$_2$, —SO$_2$NH—C$_1$-C$_6$-alkyl, —SO$_2$NH-aryl, —SO$_2$NH-heteroaryl, —C$_1$-C$_6$-alkyl, —C$_3$-C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$-C$_6$-alkoxy, methoxymethoxy, methoxyethoxy, amino, benzylamino, arylamino, heteroarylamino, —C$_1$-C$_3$-alkylamino, arylthio, heteroarylthio, benzylthio, —C$_1$-C$_6$-alkylthio, or methylthiomethyl;

substituted heteroaryl is a heteroaryl group substituted by independent replacement of one, two or three of the hydrogen atoms thereon with —F, —Cl, —Br, —I, —OH, —NO$_2$, —CN, —C(O)—C$_1$-C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$-C$_6$-alkyl, —CONH-aryl, —CONH-heteroaryl, —OC(O)—C$_1$-C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$-C$_6$-alkyl, —OCONH-aryl, —OCONH-heteroaryl, —NHC(O)—C$_1$-C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$-C$_6$-alkyl, —NHCONH-aryl, —NHCONH-heteroaryl, —SO$_2$—C$_1$-C$_6$-alkyl, —SO$_2$-aryl, —SO$_2$-heteroaryl, —SO$_2$NH$_2$, —SO$_2$NH—C$_1$-C$_6$-alkyl, —SO$_2$NH-aryl, —SO$_2$NH-heteroaryl, —C$_1$-C$_6$-alkyl, —C$_3$-C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$-C$_6$-alkoxy, methoxymethoxy, methoxyethoxy, amino, benzylamino, arylamino, heteroarylamino, —C$_1$-C$_3$-alkylamino, arylthio, heteroarylthio, benzylthio, —C$_1$-C$_6$-alkylthio, or methylthiomethyl; and substituted heterocycloalkyl is a heterocycloalkyl group substituted by independent replacement of one, two or three of the hydrogen atoms thereon with —F, —Cl, —Br, —I, —OH, —NO$_2$, —CN, —C(O)—C$_1$-C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$-C$_6$-alkyl, —CONH-aryl, —CONH-heteroaryl, —OC(O)—C$_1$-C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$-C$_6$-alkyl, —OCONH-aryl, —OCONH-heteroaryl, —NHC(O)—C$_1$-C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$-C$_6$-alkyl, —NHCONH-aryl, —NHCONH-heteroaryl, —SO$_2$—C$_1$-C$_6$-alkyl, —SO$_2$-aryl, —SO$_2$-heteroaryl, —SO$_2$NH$_2$, —SO$_2$NH—C$_1$-C$_6$-alkyl, —SO$_2$NH-aryl, —SO$_2$NH-heteroaryl, —C$_1$-C$_6$-alkyl, —C$_3$-C$_6$-cycloalkyl, —CF$_3$, —CH$_2$CF$_3$, —CHCl$_2$, —CH$_2$OH, —CH$_2$CH$_2$OH$_2$, —CH$_2$NH$_2$, —CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, —C$_1$-C$_3$-alkylamino, arylthio, heteroarylthio, benzylthio, alkylthio, or methylthiomethyl.

2. A compound according to claim 1, wherein R$^2$ is hydrogen, R$^3$ is —OR$^{13}$, and R$^{13}$ is hydrogen.

3. A compound according to claim 1, wherein R$^2$ and R$^3$ together are oxo.

4. A compound according to claim 1, wherein R$^4$ and R$^5$ are hydrogen.

5. A compound according to claim 1, wherein R$^4$ and R$^5$ together are —C(O)—.

6. A compound according to claim 1, wherein R$^6$ is hydrogen.

7. A compound according to claim 1, wherein R$^6$ is methyl.

8. A compound according to claim 1, wherein R$^1$ is —CH$_2$—CH=CH$_2$ or —CH$_2$—CH=CH-(3-quinolinyl).

9. A compound according to claim 8, wherein R$^1$ is —CH$_2$—CH=CH$_2$.

10. A compound according to claim 8, wherein R$^1$ is —CH$_2$—CH=CH-(3-quinolinyl).

11. A method for preparing compounds selected from the group consisting of compounds of formula (I)

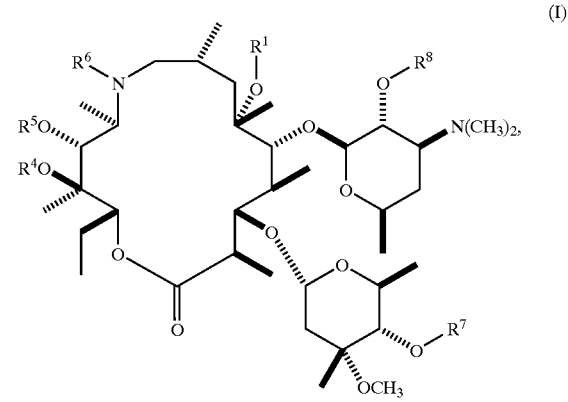

compounds of formula (II)

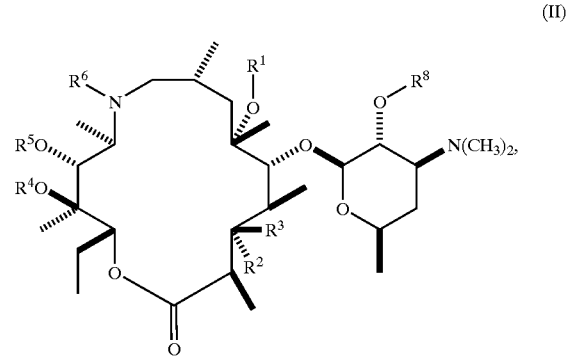

compounds of formula (III)

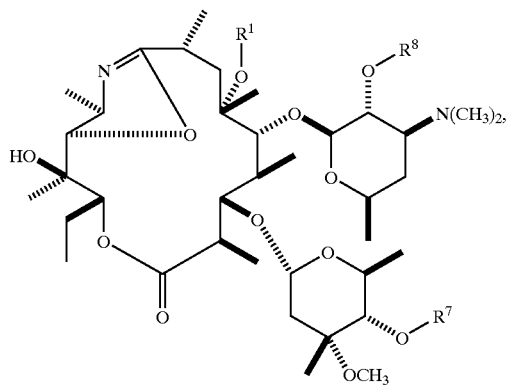

and
compounds of formula (IV)

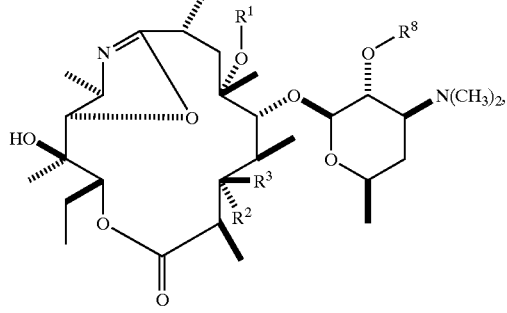

or pharmaceutically acceptable salts thereof, wherein, in formulas (I)–(IV), $R^1$ is selected from the group consisting of
(1) —$C_3$–$C_{12}$-alkenyl, and
(2) —$C_3$–$C_{12}$-alkynyl,
wherein (1)–(2) can be optionally substituted with one, two, or three substituents independently selected from the group consisting of
(a) halogen,
(b) —$OR^9$, wherein $R^9$ is selected from the group consisting of
 (i) hydrogen,
 (ii) —$C_1$–$C_{12}$-alkyl,
 (iii) —$C_2$–$C_{12}$-heteroalkyl,
 wherein (ii) and (iii) can be optionally substituted with one, two, or three substituents independently selected from the group consisting of
  (1') aryl,
  (2') substituted aryl,
  (3') heteroaryl, and
  (4') substituted heteroaryl,
 (iv) aryl,
 (v) substituted aryl,
 (vi) heteroaryl, and
 (xv) substituted heteroaryl,
(c) —$NR^{11}R^{12}$, wherein $R^{11}$ and $R^{12}$ are independently selected from the group consisting of
 (i) hydrogen,
 (ii) —$C_1$–$C_{12}$-alkyl,
 (iii) —$C_2$–$C_{12}$-heteroalkyl,
 wherein (ii) and (iii) can be optionally substituted with one, two, or three substituents independently selected from the group consisting of
  (1') aryl,
  (2') substituted aryl,
  (3') heteroaryl, and
  (4') substituted heteroaryl,
 (iv) aryl,
 (v) substituted aryl,
 (vi) heteroaryl, and
 (xv) substituted heteroaryl, or
$R^{11}$ and $R^{12}$, together with the atom to which they are attached, form a heterocycloalkyl ring, wherein the heterocycloalkyl ring can be optionally substituted,
(d) =N—O—$R^9$, wherein $R^9$ is defined above,
(e) aryl,
(f) substituted aryl,
(g) heteroaryl,
(h) substituted heteroaryl,
(i) —$C_3$–$C_8$-cycloalkyl,
(j) heterocycloalkyl,
(k) substituted heterocycloalkyl,
(l) —$NHC(O)R^9$, wherein $R^9$ is defined above,
(m) —$NHC(O)OR^{10}$, wherein $R^{10}$ is selected from the group consisting of
 (i) —$C_1$–$C_{12}$-alkyl,
 (ii) —$C_1$–$C_{12}$-heteroalkyl,
 wherein (i) and (ii) can be optionally substituted with one, two, or three substituents independently selected from the group consisting of
  (1') aryl,
  (2') substituted aryl,
  (3') heteroaryl, and
  (4') substituted heteroaryl,
 (iii) aryl,
 (iv) substituted aryl,
 (v) heteroaryl, and
 (vi) substituted heteroaryl,
(n) —$NHC(O)NR^{11}R^{12}$, wherein $R^{11}$ and $R^{12}$ are defined above,
(o) —$OC(O)R^{10}$, wherein $R^{10}$ is defined above,
(p) —$OC(O)OR^{10}$, wherein $R^{10}$ is defined above,
(q) —$OC(O)NR^{11}R^{12}$, wherein $R^{11}$ and $R^{12}$ are defined above,
(r) —$C(O)R^9$, wherein $R^9$ is defined above,
(s) —$CO_2R^9$, wherein $R^9$ is defined above, and
(t) —$C(O)NR^{11}R^{12}$, wherein $R^{11}$ and $R^{12}$ are defined above;
$R^2$ is hydrogen;
$R^3$ is —$OR^{13}$, wherein $R^{13}$ is selected from the group consisting of
(1) hydrogen,
(2) —$C(O)R^{10}$, wherein $R^{10}$ is defined above,
(3) —$CO_2R^{10}$, wherein $R^{10}$ is defined above, and
(4) —$C(O)NR^{11}R^{12}$, wherein $R^{11}$ and $R^{12}$ are defined above; or
$R^2$ and $R^3$ together are oxo;
$R^4$ and $R^5$ are hydrogen; or
$R^4$ and $R^5$ together are —C(O)— or —$(CH_2)_x$—, wherein x is one, two, or three; or
$R^5$ and $R^6$ together are —C(O)— or —$(CH_2)_x$—, wherein x is defined above;

$R^6$ is selected from the group consisting of
(1) hydrogen,
(2) —$C_1$–$C_{12}$-alkyl
(3) (1) —$C_3$–$_{12}$-alkenyl, and
(4) (2) —$C_3$–$C_{12}$-alkynyl,
wherein (1)–(4) can be optionally substituted with one, two, or three substituents independently selected from the group consisting of
(a) halogen,
(b) —$OR^9$, wherein $R^9$ is selected from the group consisting of
  (i) hydrogen,
  (ii) —$C_1$–$C_{12}$-alkyl,
  (iii) —$C_2$–$C_{12}$-heteroalkyl,
  wherein (ii) and (iii) can be optionally substituted with one, two, or three substituents independently selected from the group consisting of
    (1') aryl,
    (2') substituted aryl,
    (3') heteroaryl, and
    (4') substituted heteroaryl,
  (iv) aryl,
  (v) substituted aryl,
  (vi) heteroaryl, and
  (xv) substituted heteroaryl,
(c) —$NR^{11}R^{12}$, wherein $R^{11}$ and $R^{12}$ are independently selected from the group consisting of
  (i) hydrogen,
  (ii) —$C_1$–$C_{12}$-alkyl,
  (iii) —$C_2$–$C_{12}$-heteroalkyl,
  wherein (ii) and (iii) can be optionally substituted with one, two, or three substituents independently selected from the group consisting of
    (1') aryl,
    (2') substituted aryl,
    (3') heteroaryl, and
    (4') substituted heteroaryl,
  (iv) aryl,
  (v) substituted aryl,
  (vi) heteroaryl, and
  (xv) substituted heteroaryl, or
$R^{11}$ and $R^{12}$, together with the atom to which they are attached, form a heterocycloalkyl ring, wherein the heterocycloalkyl ring can be optionally substituted,
(d) =N—O—$R^9$, wherein $R^9$ is defined above,
(e) aryl,
(f) substituted aryl,
(g) heteroaryl
(h) substituted heteroaryl,
(i) —$C_3$–$C_8$-cycloalkyl,
(j) heterocycloalkyl,
(k) substituted heterocycloalkyl,
(l) —NHC(O)$R^9$, wherein $R^9$ is defined above,
(m) —NHC(O)O$R^{10}$, wherein $R^{10}$ is selected from the group consisting of
  (i) —$C_1$–$C_{12}$-alkyl,
  (ii) —$C_1$–$C_{12}$-heteroalkyl,
  wherein (i) and (ii) can be optionally substituted with one, two, or three substituents independently selected from the group consisting of
    (1') aryl,
    (2') substituted aryl,
    (3') heteroaryl, and
    (4') substituted heteroaryl,
  (iii) aryl,
  (iv) substituted aryl,
  (v) heteroaryl, and
  (vi) substituted heteroaryl,
(n) —NHC(O)$NR^{11}R^{12}$, wherein $R^{11}$ and $R^{12}$ are defined above,
(o) —OC(O)$R^{10}$, wherein $R^{10}$ is defined above,
(p) —OC(O)O$R^{10}$, wherein $R^{10}$ is defined above,
(q) —OC(O)$NR^{11}R^{12}$, wherein $R^{11}$ and $R^{12}$ are defined above,
(r) —C(O)$R^9$, wherein $R^9$ is defined above,
(s) —$CO_2R^9$, wherein $R^9$ is defined above, and
(t) —C(O)$NR^{11}R^{12}$, wherein $R^{11}$ and $R^{12}$ are defined above;

$R^7$ is selected from the group consisting of
(1) hydrogen,
(2) —$C_1$–$C_{12}$-alkyl,
(3) —$C_3$–$C_{12}$-alkenyl,
(4) —$C_3$–$C_{12}$-alkynyl,
(5) —$C_2$–$C_{12}$-heteroalkyl,
(6) —$C_4$–$C_{12}$-heteroalkenyl,
(7) —$C_4$–$C_{12}$-heteroalkynyl,
wherein (2)–(7) can be optionally substituted with one, two, or three substituents independently selected from the group consisting of
(a) halo,
(b) hydroxy,
(c) —$NR^{11}R^{12}$, wherein $R^{11}$ and $R^{12}$ are defined above,
(d) aryl,
(e) substituted aryl,
(f) heteroaryl, and
(g) substituted heteroaryl,
(8) —C(O)$R^9$, wherein $R^9$ is defined above,
(9) —$CO_2R^9$, wherein $R^9$ is defined above, and
(11) —C(O)$NR^{11}R^{12}$, wherein $R^{11}$ and $R^{12}$ are defined above; and $R^8$ is hydrogen or a hydroxy protecting group;
wherein substituted aryl is an aryl group substituted by independent replacement of one, two, or three of the hydrogen atoms thereon with —F, —Cl, —Br, —I, —OH, —$NO_2$, —CN, —C(O)—$C_1$–$C_6$-alkyl, —C(O)-aryl, —C(O)-heteroaryl, —$CO_2$-alkyl, —$CO_2$-aryl, —$CO_2$-heteroaryl, —$CONH_2$, —CONH—$C_1$–$C_6$-alkyl, —CONH-aryl, —CONH-heteroaryl, —OC(O)—$C_1$–$C_6$-alkyl, —OC(O)-aryl, —OC(O)-heteroaryl, —$OCO_2$-alkyl, —$OCO_2$-aryl, —$OCO_2$-heteroaryl, —$OCONH_2$, —OCONH—$C_1$–$C_6$-alkyl, —OCONH-aryl, —OCONH-heteroaryl, —NHC(O)—$C_1$–$C_6$-alkyl, —NHC(O)-aryl, —NHC(O)-heteroaryl, —$NHCO_2$-alkyl, —$NHCO_2$-aryl, —$NHCO_2$-heteroaryl, —$NHCONH_2$, —NHCONH—$C_1$–$C_6$-alkyl, —NHCONH-aryl, —NHCONH-heteroaryl, —$SO_2$—$C_1$–$C_6$-alkyl, —$SO_2$-aryl, —$SO_2$-heteroaryl, —$SO_2NH_2$, —$SO_2$NH—$C_1$–$C_6$-alkyl, —$SO_2$NH-aryl, —$SO_2$NH-heteroaryl, —$C_1$–$C_6$-alkyl, —$C_3$–$C_6$- cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxy, methoxymethoxy, methoxyethoxy, amino, benzylamino, arylamino, heteroarylamino, —C$_1$–C$_3$-alkylamino, arylthio, heteroarylthio, benzylthio, —C$_1$–C$_6$-alkylthio, or methylthiomethyl;

substituted heteroaryl is a heteroaryl group substituted by independent replacement of one, two or three of the hydrogen atoms thereon with —F, —Cl, —Br, —I, —OH, —NO$_2$, —CN, —C(O)—C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$–C$_6$-alkyl, —CONH-aryl, —CONH-heteroaryl, —OC(O)—C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$–C$_6$-alkyl, —OCONH-aryl, —OCONH-heteroaryl, —NHC(O)—C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$–C$_6$-alkyl, —NHCONH-aryl, —NHCONH-heteroaryl, —SO$_2$—C$_1$–C$_6$-alkyl, —SO$_2$-aryl, —SO$_2$-heteroaryl, —SO$_2$NH$_2$, —SO$_2$NH—C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, —C$_1$–C$_6$-alkoxy, methoxymethoxy, methoxyethoxy, amino, benzylamino, arylamino, heteroarylamino, —C$_1$–C$_3$-alkylamino, arylthio, heteroarylthio, benzylthio, —C$_1$–C$_6$-alkylthio, or methylthiomethyl; and substituted heterocycloalkyl is a heterocycloalkyl group substituted by independent replacement of one, two or three of the hydrogen atoms thereon with —F, —Cl, —Br, —I, —OH, —NO$_2$, —CN, —C(O)—C$_1$–C$_6$-alkyl, —C(O)-aryl, —C(O)-heteroaryl, —CO$_2$-alkyl, —CO$_2$-aryl, —CO$_2$-heteroaryl, —CONH$_2$, —CONH—C$_1$–C$_6$-alkyl, —CONH-aryl, —CONH-heteroaryl, —OC(O)—C$_1$–C$_6$-alkyl, —OC(O)-aryl, —OC(O)-heteroaryl, —OCO$_2$-alkyl, —OCO$_2$-aryl, —OCO$_2$-heteroaryl, —OCONH$_2$, —OCONH—C$_1$–C$_6$-alkyl, —OCONH-aryl, —OCONH-heteroaryl, —NHC(O)—C$_1$–C$_6$-alkyl, —NHC(O)-aryl, —NHC(O)-heteroaryl, —NHCO$_2$-alkyl, —NHCO$_2$-aryl, —NHCO$_2$-heteroaryl, —NHCONH$_2$, —NHCONH—C$_1$–C$_6$-alkyl, —NHCONH-aryl, —NHCONH-heteroaryl, —SO$_2$—C$_1$–C$_6$-alkyl, —SO$_2$-aryl, —SO$_2$-heteroaryl, —SO$_2$NH$_2$, —SO$_2$NH—C$_1$–C$_6$-alkyl, —SO$_2$NH-aryl, —SO$_2$NH-heteroaryl, —C$_1$–C$_6$-alkyl, —C$_3$–C$_6$-cycloalkyl, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, aryl, heteroaryl, benzyl, benzyloxy, aryloxy, heteroaryloxy, alkoxy, methoxymethoxy, methoxyethoxy, amino, benzylamino, arylamino, heteroarylamino, —C$_1$–C$_3$-alkylamino, arylthio, heteroarylthio, benzylthio, alkylthio, or methylthiomethyl;

the method comprising (a) reacting compounds of formula (Ia)

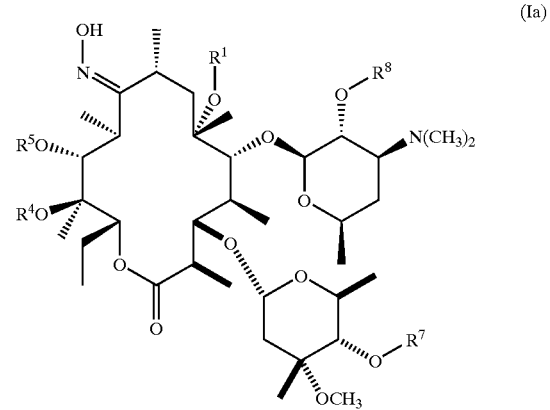

(Ia)

or compounds of formula (Ib)

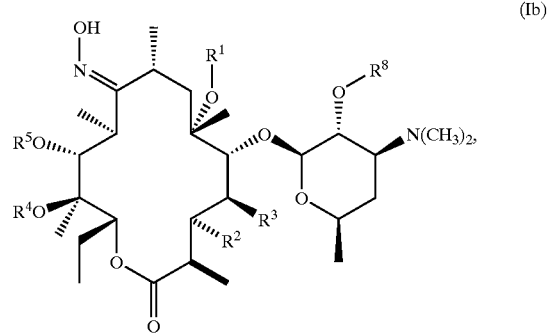

(Ib)

with an oxime activating agent;

(b) reacting the product from step (a) with a reducing agent;

(c) optionally alkylating the product from step (b); and (d) optionally deprotecting the product from step (c).

12. The method according to claim 11, wherein the oxime activating agent is a sulfonyl halide.

13. The method according to claim 12, wherein the sulfonyl halide is para-toluenesulfonyl chloride, methanesulfonyl chloride, para-bromosulfonyl chloride, or para-bromosulfonyl chloride.

14. The method according to claim 11, wherein the reducing agent is borane in tetrahydrofuran, borane dimethyl sulfide, sodium cyanoborohydride, or sodium borohydride, optionally in the presence of an acid.

15. The method according to claim 14, wherein the reducing agent is sodium cyanoborohydride in the presence of acid.

16. The method according to claim 15, wherein the acid is acetic acid.

17. A pharmaceutical composition comprising a pharmaceutically effective amount of a compound of claim 1 in combination with a pharmaceutically acceptable carrier.

18. A method of treating a bacterial infection in a mammal in need of such treatment which comprises administering to the mammal a therapeutically effective amount of a compound of claim 1.

19. A compound selected from the group consisting of

Compound of formula (III): $R^1$ is —$CH_2CH$=$CH_2$, $R^4$ is hydrogen, $R^7$ is hydrogen, $R^8$ is hydrogen, Compound of formula (I): $R^1$ is —$CH_2CH$=$CH_2$, $R^4$ is hydrogen, $R^5$ is hydrogen, $R^6$ is hydrogen, $R^7$ is hydrogen, $R^8$ is hydrogen, Compound of formula (I): $R^1$ is —$CH_2CH$=$CH_2$, $R^4$ is hydrogen, $R^5$ is hydrogen, $R^6$ is methyl, $R^7$ is hydrogen, $R^8$ is hydrogen, Compound of formula (II): $R^1$ is —$CH_2CH$=$CH$-(3-quinolinyl), $R^2$ and $R^3$ together are oxo, $R^4$ is hydrogen, $R^5$ is hydrogen, $R^6$ is methyl, $R^8$ is hydrogen, Compound of formula (II): $R^1$ is —$CH_2CH$=$CH$-(3-quinolinyl), $R^2$ and $R^3$ together are oxo, $R^4$ is hydrogen, $R^5$ is hydrogen, $R^6$ is methyl, $R^8$ is hydrogen, Compound of formula (II): $R^1$ is —$CH_2CH$=$CH$-(3-quinolinyl), $R^2$ and $R^3$ together are oxo, $R^4$ and $R^5$ together are —C(O)—, $R^6$ is methyl, $R^8$ is —C(O)$CH_3$, and Compound of formula (I): $R^1$ is —$CH_2CH$=$CH$-(3-quinolinyl), $R^4$ is hydrogen, $R^5$ is hydrogen, $R^6$ is methyl, $R^7$ is hydrogen, $R^8$ is hydrogen.

* * * * *